United States Patent
Ogawa et al.

(10) Patent No.: US 7,932,100 B2
(45) Date of Patent: Apr. 26, 2011

(54) METHOD FOR DETECTING TARGET SUBSTANCE AND TARGET-SUBSTANCE DETECTION KIT

(75) Inventors: Miki Ogawa, Machida (JP); Masato Minami, Yokohama (JP); Takeshi Imamura, Chigasaki (JP); Takashi Ikeda, Yokohama (JP); Kazumichi Nakahama, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 146 days.

(21) Appl. No.: 12/162,789

(22) PCT Filed: Mar. 30, 2007

(86) PCT No.: PCT/JP2007/057712
§ 371 (c)(1),
(2), (4) Date: Jul. 30, 2008

(87) PCT Pub. No.: WO2007/114512
PCT Pub. Date: Oct. 11, 2007

(65) Prior Publication Data
US 2009/0000360 A1    Jan. 1, 2009

(30) Foreign Application Priority Data

Mar. 31, 2006  (JP) .................................. 2006-100683
Nov. 24, 2006  (JP) .................................. 2006-317401

(51) Int. Cl.
*G01N 33/553* (2006.01)
(52) U.S. Cl. ........ 436/526; 436/518; 436/524; 436/525; 436/807; 435/283.1; 435/287.1; 435/287.2
(58) Field of Classification Search .................. 436/518, 436/524, 525, 526, 807; 435/7.1, 283.1, 435/287.1, 287.2, 287.9, 288.3
See application file for complete search history.

(56) References Cited

U.S. PATENT DOCUMENTS 5,665,597 A    9/1997    Imamura et al.
(Continued)

FOREIGN PATENT DOCUMENTS

JP    2001033455    2/2001
(Continued)

OTHER PUBLICATIONS

PCT International Search Report and Written Opinion of the International Searching Authority in International Application No. PCT/JP2007/057712, mailing date Jul. 10, 2007.
(Continued)

*Primary Examiner* — Melanie J Yu
(74) *Attorney, Agent, or Firm* — Fitzpatrick, Cella, Harper & Scinto

(57) ABSTRACT

The present invention provides a method for detecting a target substance by detecting the presence or concentration of a target substance in a sample solution by bringing the sample solution into contact with a detecting element including a detecting part and a non-detecting part and detecting the presence or number of a magnetic label (magnetic marker) present in the vicinity of the surface of the detecting part and provides a target-substance detection kit. The surface potential $\psi_1$ of the magnetic label in the sample solution, the surface potential $\psi_2$ of the detecting parts and the surface potential $\psi_3$ of the non-detecting part satisfy any one of the following relationships i) to iv):

i) $\psi_1\psi_3>0$ and $\psi_2=0$,
ii) $\psi_1\psi_2<0$ and $\psi_3=0$,
iii) $\psi_1\psi_2<0$, $\psi_2\psi_3>0$, and $|\psi_2|>|\psi_3|$, and
iv) $\psi_1\psi_2<0$ and $\psi_2\psi_3<0$; and the target substance borne by the magnetic label is captured by a primary capturing body borne by the detecting part, or the target substance captured by a primary capturing body borne by the detecting part is captured by a secondary capturing body borne by the magnetic label.

4 Claims, 5 Drawing Sheets

U.S. PATENT DOCUMENTS

| | | | |
|---|---|---|---|
| 5,679,568 A | 10/1997 | Imamura et al. | |
| 5,693,527 A | 12/1997 | Imamura et al. | |
| 5,803,664 A | 9/1998 | Kawabata et al. | |
| 5,807,736 A | 9/1998 | Kozaki et al. | |
| 5,854,059 A | 12/1998 | Kozaki et al. | |
| 5,863,789 A | 1/1999 | Komatsu et al. | |
| 5,945,331 A | 8/1999 | Kozaki et al. | |
| 5,962,305 A | 10/1999 | Mihara et al. | |
| 5,981,297 A | 11/1999 | Baselt | |
| 5,993,658 A | 11/1999 | Kato et al. | |
| 6,004,772 A | 12/1999 | Imamura et al. | |
| 6,017,746 A | 1/2000 | Imamura et al. | |
| 6,096,530 A | 8/2000 | Kato et al. | |
| 6,319,706 B1 | 11/2001 | Kawaguchi et al. | |
| 6,472,191 B1 | 10/2002 | Yano et al. | |
| 6,479,621 B2 | 11/2002 | Honma et al. | |
| 6,548,311 B1 * | 4/2003 | Knoll | 436/524 |
| 6,586,562 B2 | 7/2003 | Honma et al. | |
| 6,649,381 B1 | 11/2003 | Honma et al. | |
| 6,660,516 B1 | 12/2003 | Imamura et al. | |
| 6,686,439 B2 | 2/2004 | Kenmoku et al. | |
| 6,770,489 B1 | 8/2004 | Enpuku et al. | |
| 6,803,444 B2 | 10/2004 | Suzuki et al. | |
| 6,808,854 B2 | 10/2004 | Imamura et al. | |
| 6,828,074 B2 | 12/2004 | Yano et al. | |
| 6,855,472 B2 | 2/2005 | Imamura et al. | |
| 6,858,367 B2 | 2/2005 | Yano et al. | |
| 6,858,417 B2 | 2/2005 | Yano et al. | |
| 6,861,496 B2 | 3/2005 | Kenmoku et al. | |
| 6,861,550 B2 | 3/2005 | Honma et al. | |
| 6,864,074 B2 | 3/2005 | Yano et al. | |
| 6,867,023 B2 | 3/2005 | Honma et al. | |
| 6,869,782 B2 | 3/2005 | Kenmoku et al. | |
| 6,908,720 B2 | 6/2005 | Kenmoku et al. | |
| 7,169,598 B2 | 1/2007 | Honma et al. | |
| 7,262,281 B2 | 8/2007 | Sleytr et al. | |
| 7,354,995 B2 | 4/2008 | Imamura et al. | |
| 7,387,901 B2 | 6/2008 | Nishiuma et al. | |
| 7,403,287 B2 | 7/2008 | Ogawa et al. | |
| 7,425,455 B2 | 9/2008 | Fukumoto et al. | |
| 2002/0132372 A1 | 9/2002 | Enpuku | |
| 2004/0137527 A1 | 7/2004 | Sleytr et al. | |
| 2005/0106758 A1 | 5/2005 | Fukumoto et al. | |
| 2006/0188398 A1 | 8/2006 | Yano et al. | |
| 2006/0251610 A1 | 11/2006 | Nakahama | |
| 2007/0105087 A1 | 5/2007 | Ban et al. | |
| 2007/0178522 A1 | 8/2007 | Shiotsuka et al. | |
| 2007/0231926 A1 | 10/2007 | Ikeda | |
| 2007/0237673 A1 | 10/2007 | Ideka et al. | |
| 2007/0248987 A1 | 10/2007 | Imamura et al. | |
| 2007/0298510 A1 | 12/2007 | Imamura et al. | |
| 2008/0000308 A1 | 1/2008 | Kikuchi et al. | |
| 2008/0108123 A1 | 5/2008 | Imamura et al. | |
| 2008/0108132 A1 | 5/2008 | Ban et al. | |
| 2008/0117423 A1 | 5/2008 | Ogawa et al. | |
| 2008/0187461 A1 | 8/2008 | Hatakeyama et al. | |
| 2008/0206784 A1 | 8/2008 | Shiotsuka et al. | |
| 2008/0225292 A1 | 9/2008 | Nishiuma et al. | |
| 2008/0241964 A1 | 10/2008 | Kaieda et al. | |
| 2008/0309323 A1 | 12/2008 | Okano et al. | |

FOREIGN PATENT DOCUMENTS

| | | |
|---|---|---|
| JP | 2003000241 | 1/2003 |
| JP | 2005500026 | 1/2005 |
| JP | 2005091014 | 4/2005 |
| WO | 03067258 | 8/2003 |

OTHER PUBLICATIONS

U.S. Appl. No. 11/995,991, International filing date Sep. 1, 2008, Imamura, et al.

U.S. Appl. No. 12/180,391, filed Jul. 25, 2008, Takashi Ikeda.

U.S. Appl. No. 12/145,451, filed Jun. 24, 2008, Ban, et al.

U.S. Appl. No. 12/188,166, filed Aug. 7, 2008, Minami, et al.

U.S. Appl. No. 12/065,720, International filing date Oct. 3, 2006, Ban, et al.

U.S. Appl. No. 12/120,514, filed May 14, 2008, Takashi Ikeda.

U.S. Appl. No. 12/160,987, International filing date Mar. 13, 2007, Miki Ogawa.

U.S. Appl. No. 10/548,442, International filing date Aug. 18, 2004, Shiotsuka, et al.

* cited by examiner

METHOD FOR DETECTING TARGET SUBSTANCE AND TARGET-SUBSTANCE DETECTION KIT

TECHNICAL FIELD

The present invention relates to a method for detecting a target substance in a sample solution and relates to a target-substance detection kit. Specifically, the present invention relates to a method for detecting a target substance and a target-substance detection kit which can be suitably applied to a so-called biosensor utilizing the specific molecular recognition ability of a substance of biological origin or its analogue.

BACKGROUND ART

Biosensors are a measurement device utilizing excellent molecular recognition ability of living organisms or biomolecules. As pairs of affinity binding partners in living organisms, for example, enzyme-substrate, antigen-antibody, and DNA-DNA are known. Biosensors utilize the principle that one of these pairs can be selectively measured by using the other of the pair immobilized or supported on a substrate. Recently, biosensors have been expected to be broadly used not only in the field of medicine but also in the fields of environment and food. Consequently, in order to broaden the application fields of biosensors, highly sensitive and highly efficient biosensors which can be installed at every place or which are reduced in size and weight so as to be portable are expected.

As one of methods detecting such biomolecular interactions, the magnetic detection method utilizing a magnetic label is now under active development and used in solid-phase analysis.

FIG. 1 illustrates an example of the conventional solid-phase analysis using a magnetic label. In the method shown in FIG. 1, a primary capturing body 3 (called a primary antibody when an antigen is detected by utilizing an antigen-antibody reaction) which can specifically recognize and capture a region (called an epitope when the target substance is an antigen and the antigen is detected by utilizing an antigen-antibody reaction) of a target substance 5 is previously immobilized on a surface of a substrate 1. Then, a sample solution containing the target substance 5 is brought into contact with the surface of the substrate 1. With this process, the target substance 5 is specifically captured by the primary capturing body 3. Then, a magnetic label 9 provided with a secondary capturing body 4 (called a secondary antibody when an antigen is detected by utilizing an antigen-antibody reaction) is added to the sample solution. The secondary capturing body 4 can specifically recognize and capture a region, of the target substance 5, other than the region which is specifically captured by the primary capturing body 3. (Here, the magnetic label 9 includes a magnetic structure 2 and a secondary capturing body 4 immobilized on the surface of the magnetic structure 2.) With this process, the secondary capturing body 4 recognizes and captures the target substance 5 specifically captured by the primary capturing body 3 immobilized on the surface of the substrate 1. Consequently, the magnetic label is apparently captured by the target substance. Accordingly, as shown in FIG. 1, the magnetic label is immobilized in the vicinity of the surface of the substrate 1 via the target substance 5.

In addition, as a method different from the above, the following method is also known. A magnetic label 2 provided with a secondary capturing body 4 is added to a sample solution containing the target substance 5 to form a complex of "the target substance and the secondary capturing body on the magnetic label". Then, the resulting complex is brought into contact with a primary capturing body 3 immobilized on a substrate 1. As a result, as shown in FIG. 1, the magnetic label can be immobilized on the surface of the substrate via the target substance.

Lastly, the number of the magnetic label immobilized on the surface of a detecting element is measured by any method and thereby the number or concentration of the target substance to be determined can be calculated.

As a target-substance detecting element using such a magnetic detection technology, Japanese Patent Application Laid-Open No. 2001-033455 discloses an immunoassay for detecting a target substance by using a magnetic material as a label. The label is bound to the target substance in a sample solution by an antigen-antibody reaction and is magnetized and detected using a superconducting quantum interference device (SQUID) as a magnetic sensor.

Further, International Publication No. WO 03/067258 discloses a biosensor for analyzing an object to be measured using detecting elements for detecting a magnetic field produced by bound magnetic molecules and having semiconductor hall devices. The analysis is conducted based on the amount of the specified magnetic molecules.

U.S. Pat. No. 5,981,297 discloses a method for detecting a magnetic signal of fine magnetic particles using a magnetoresistive element. A primary capture molecule on a sensor element is bound to a secondary capture molecule labeled with the fine magnetic particles as a signal via a target molecule.

The above-described methods are biosensing methods utilizing magnetic labels. In the meantime, Japanese Patent Application Laid-Open No. 2005-91014 discloses a biosensing method using a substrate provided with a biomolecule-immobilizing region and a template region surrounding the biomolecule-immobilizing region. The template region is covered with a monomolecular layer which does not react with the target molecule and a capture molecule. Such a structure is aimed to stably generate a signal which is derived from biomolecular interaction between a target molecule and a capture molecule and to detect the signal with a high accuracy and high sensitivity.

However, biosensors still have challenges to achieve further higher sensitivity and accuracy (a decrease in noise) and to reduce reaction time, namely, to improve the detection efficiency.

DISCLOSURE OF THE INVENTION

The present invention provides a method for detecting a target substance with excellent detection efficiency and a high sensitivity and provides a target-substance detection kit.

The present invention provides a method for detecting a target substance in a sample solution by using a detecting element including a detecting part provided with a primary capturing body on the surface thereof and a non-detecting part and by detecting a magnetic label present in the vicinity of the detecting part.

In the method according to the present invention, the surface potential $\psi_1$ of the magnetic label in the sample solution, the surface potential $\psi_2$ of the detecting part, and the surface potential $\psi_3$ of the non-detecting part satisfy any one of the following relationships i) to iv):

$\psi_1\psi_3>0$ and $\psi_2=0$,  i)

$\psi_1\psi_2<0$ and $\psi_3=0$,  ii)

$\psi_1\psi_2<0$, $\psi_2\psi_3>0$, and $|\psi_2|>|\psi_3|$, and  iii)

$\psi_1\psi_2<0$ and $\psi_2\psi_3<0$;  iv)

the target substance borne by the magnetic label is captured by the primary capturing body borne by the detecting part, or the target substance captured by the primary capturing body borne by the detecting part is captured by a secondary capturing body borne by the magnetic label.

The present invention further provides a target-substance detection kit for detecting a target substance by detecting a magnetic label present in the vicinity of a detecting part of a detecting element including the detecting part provided with a primary capturing body on the surface thereof and a non-detecting part.

In the kit according to the present invention, the surface potential $\psi_1$ of the magnetic label in the sample solution, the surface potential $\psi_2$ of the detecting part, and the surface potential $\psi_3$ of the non-detecting part satisfy any one of the following relationships i) to iv):

$\psi_1\psi_3>0$ and $\psi_2=0$,  i)

$\psi_1\psi_2<0$ and $\psi_3=0$,  ii)

$\psi_1\psi_2<0$, $\psi_2\psi_3>0$, and $|\psi_2|>|\psi_3|$, and  iii)

$\psi_1\psi_2<0$ and $\psi_2\psi_3<0$;  iv)

the target substance borne by the magnetic label is captured by the primary capturing body borne by the detecting part, or the target substance captured by the primary capturing body borne by the detecting part is captured by a secondary capturing body borne by the magnetic label.

The relationships i) to iv) are preferably satisfied by forming a layer on any surface of the magnetic label, the detecting part, and the non-detecting part the surface potentials of which do not satisfy any one of relationships i) to iv).

Preferably, the magnetic label and the non-detecting part each have such a layered structure and the outermost layer of the magnetic label having the layered structure and the outermost layer of the non-detecting part having the layered structure are formed of the same material.

The layers formed of the same material are preferably formed of a graft polymer.

The surface potential of the detecting part is preferably generated by a voltage or current supplied from a power supply source connected to the detecting part.

The detecting part preferably has a terminal for applying a voltage or current.

Further futures of the present invention will become apparent from the following description of exemplary embodiments with reference to the attached drawings.

BEST MODE FOR CARRYING OUT THE INVENTION

Figure 1:
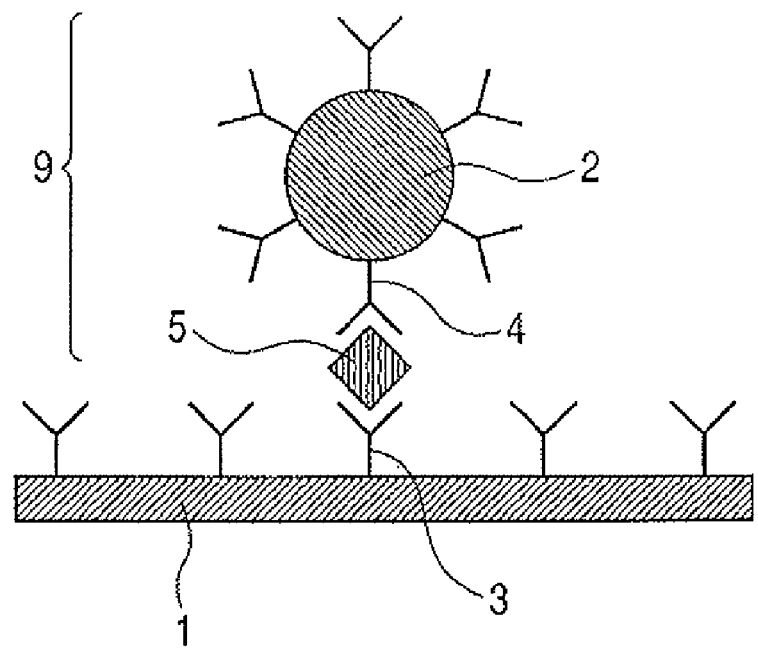
FIG. 1 is a diagram illustrating the conventional solid-phase analysis using a magnetic label.
Figure 2:
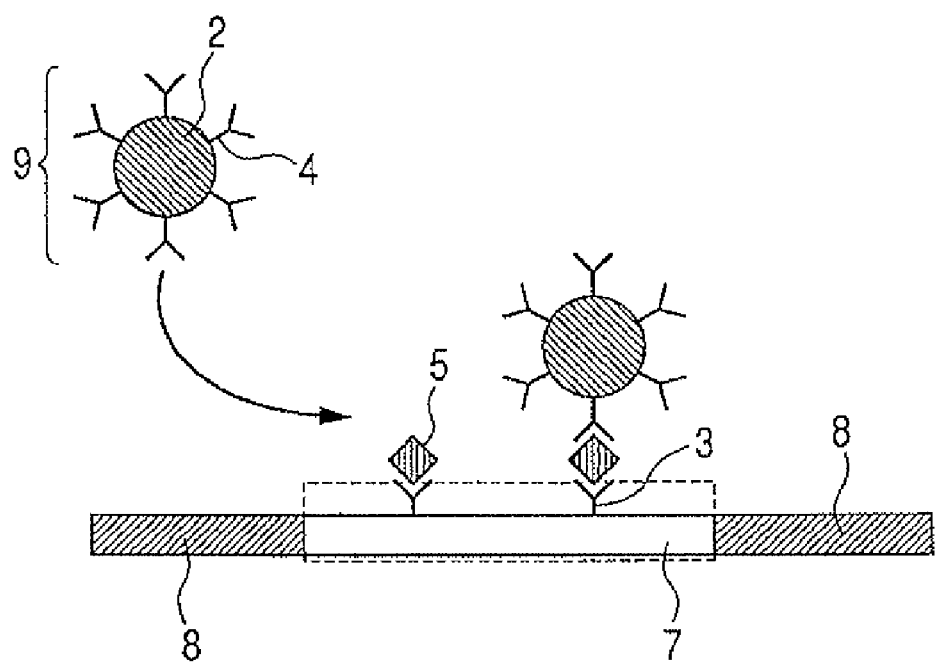
FIG. 2 is a schematic diagram illustrating a relationship between a magnetic label and a detecting element according to an embodiment.
Figure 3:
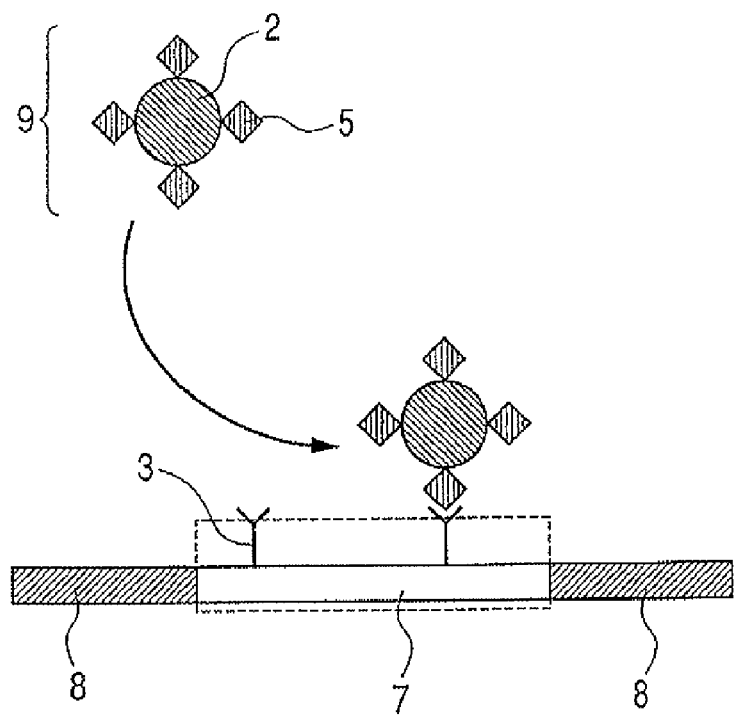
FIG. 3 is a schematic diagram illustrating a relationship between a detecting element and a magnetic label according to an embodiment, the detecting element including a non-detecting part and a detecting part and the magnetic label being provided with a target substance on the surface thereof.
Figure 4:
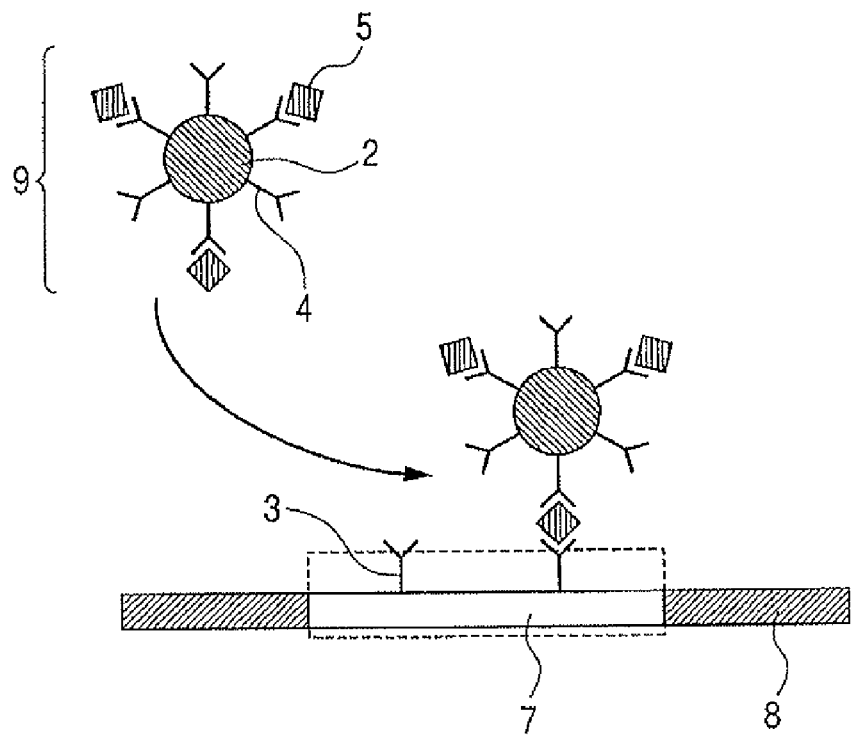
FIG. 4 is a schematic diagram illustrating a relationship between a detecting element and a magnetic label according to an embodiment, the detecting element including a non-detecting part and a detecting part and the magnetic label being provided with a secondary capturing body capturing a target substance.

FIGS. 2 to 4 are drawings schematically illustrating magnetic labels and detecting elements used for detection methods according to embodiments of the present invention, the magnetic labels and detecting elements being classified according to the difference in the target-substance detection methods. Reference numeral 2 denotes a magnetic structure, reference numeral 3 denotes a primary capturing body, reference numeral 4 denotes a secondary capturing body, reference numeral 5 denotes a target substance, reference numeral 7 denotes a detecting part, reference numeral 8 denotes a non-detecting part, and reference numeral 9 denotes a magnetic label. In these embodiments, the magnetic label 9 includes a magnetic structure 2 and a secondary capturing body 4 provided on the surface thereof. FIG. 2 illustrates a configuration in which a magnetic label is provided with a secondary capturing body on the surface thereof, FIG. 3 illustrates a configuration in which a magnetic label is provided with a target substance on the surface thereof, and FIG. 4 illustrates a configuration in which a magnetic label is provided with a secondary capturing body capturing a target substance on the surface thereof.

The configuration shown in FIG. 2 and the configuration shown in FIG. 4 are the same in that a magnetic label is provided with a secondary capturing body on the surface thereof. However, from the viewpoint of a target-substance detection method, the configuration shown in FIG. 2 is one that a target substance captured by a primary capturing body is captured by a secondary capturing body borne by the magnetic label, but the configuration shown in FIG. 4 is one that a target substance borne by a magnetic label is captured by a primary capturing body. Similarly, from the viewpoint of a target-substance detection method, the configuration shown in FIG. 3 and the configuration shown in FIG. 4 are the same in that a target substance borne by a magnetic label is captured by a primary capturing body. In addition, the structure of the detecting part and the non-detecting part may be one shown in FIG. 5. In the structure shown in FIG. 5, a substrate 6 contains a region serving as a part of a detecting part and a region serving as a part of a non-detecting part. In a structure such as that shown in FIG. 5, the detecting part 7 includes a region of a substrate 1 for immobilizing a primary capturing body 3 on the surface thereof and the primary capturing body 3, and the non-detecting part 8 includes a region other than the detecting part 7 of the substrate 1 and a layer formed on the surface of the region. In addition, in the present invention, the substrate functions as a support for the entire detecting element. The substrate refers to a detecting element which is not yet provided with a primary capturing body. Therefore, the substrate is a part of the substrate, and when the substrate is constituted with one layer, the substrate is identical with the substrate.

Figure 5:
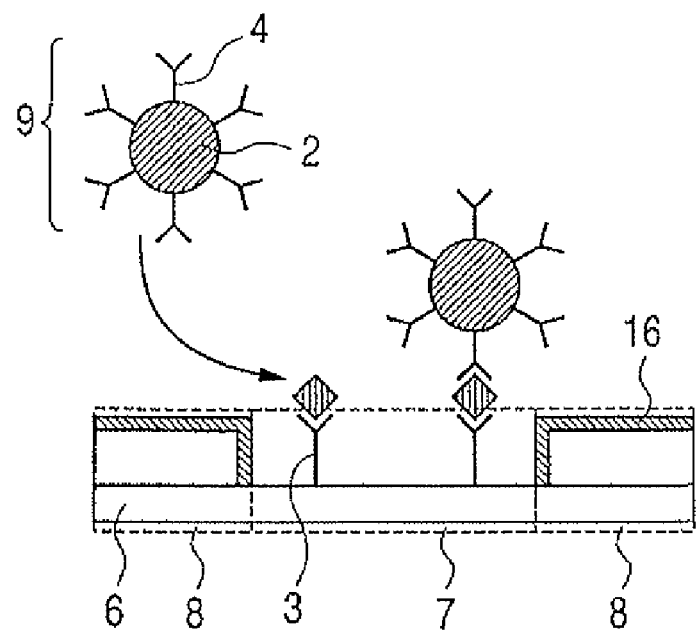
FIG. 5 is a schematic diagram illustrating a relationship between a detecting element and a magnetic label according to an embodiment, the detecting element including a detecting part and a non-detecting part having a coating layer on the surface thereof.
Figure 6:
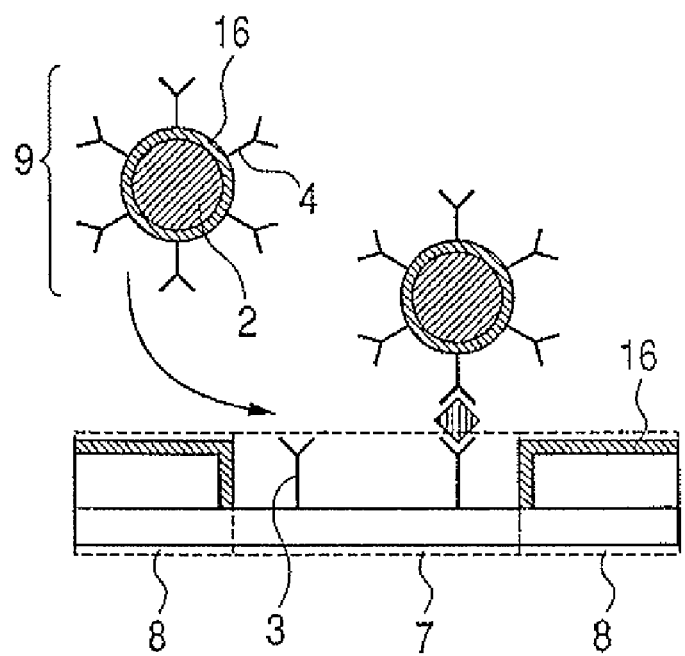
FIG. 6 is a schematic diagram illustrating a relationship between a detecting element and a magnetic label according to an embodiment, the detecting element including a detecting part and a non-detecting part having a coating layer on the surface thereof and the magnetic layer having a coating layer on the surface thereof.

Furthermore, in the embodiment shown in FIG. 5, a plurality of layers are formed on the surface of the substrate 6 at a region other than the region serving as the detecting part 7. In the drawings, the outermost layer among the plurality of layers is shown as a coating layer 16. The magnetic label may have a structure, as shown in FIG. 6, in which a coating layer 16 is provided on the surface of a magnetic structure 2 and a secondary capturing body 4 is provided on the coating layer.

In the present invention, a sample solution is brought into contact with a detecting element including a detecting part and a nondetecting part. The presence or concentration of a target substance in the sample solution is measured by detecting the presence or the number of the magnetic label (magnetic marker) remaining in the vicinity of the surface of the detecting part.

On this occasion, it is an important characteristic of the present invention that the surface potentials of the detecting part, the non-detecting part, and the magnetic label when they are in contact with the sample solution are in a relationship shown below. Further, in the present invention, the term "vicinity" denotes a range of 1 mm or less.

That is, the surface potential $\psi_1$ of the magnetic label in the sample solution, the surface potential $\psi_2$ of the detecting part, and the surface potential $\psi_3$ of the non-detecting part satisfy any one of the following relationships i) to iv):

$\psi_1\psi_3>0$ and $\psi_2=0$,      i)

$\psi_1\psi_2<0$ and $\psi_3=0$,      ii)

$\psi_1\psi_2<0$, $\psi_2\psi_3>0$, and $|\psi_2|>|\psi_3|$, and      iii)

$\psi_1\psi_2<0$ and $\psi_2\psi_3<0$;      iv)

the target substance borne by the magnetic label is captured by a primary capturing body borne by the detecting part, or the target substance captured by a primary capturing body borne by the detecting part is captured by a secondary capturing body borne by the magnetic label.

With such a characteristic, the magnetic label can be rapidly and selectively led to the vicinity of the detecting part and the detection efficiency can be improved.

In the present invention, the term "surface potential" refers to a charging condition of a surface. The "surface potential of the A" denotes the condition of the electrified surface of the A as a whole, not a local condition of the electrified surface of the A. Therefore, the surface potential of the A may be the average surface charge of the A or may be the average surface potential of the A. Further, the surface potential may be the zeta potential of the A. Furthermore, the surface potential may be the potential generated on the surface by applying a potential to the surface of the A by an external power supply. The external power supply may be connected to a reaction vessel as long as the surface potential of the detecting part can be controlled. Further, the reaction vessel itself may have a surface potential whose polarity different from that of the surface potential of the detecting part.

When an average surface charge is used as the surface potential, the surface of the A is provided with a compound containing a functional group which can become an anion or a functional group which can become a cation in a solution. In such a case, the surface potential refers to the average charge of the compound as a whole.

Therefore, the repulsive force between two materials having surface potentials is larger when the polarities of the electric potentials are the same and the absolute values is large.

Hereinafter, the magnetic label, the detecting element, and the detection kit according to the present invention will be described. Then, the conditions in the respective relationships i) to iv) will be described in detail.

In the present invention, the magnetic label is rapidly and selectively led to the vicinity of the detecting part by controlling the surface potentials of the detecting part, the non-detecting part, and the magnetic label.

<Target-Substance Detecting Element>

The target-substance detecting element used in the present invention includes a detecting part provided with a primary capturing body on the surface thereof and a non-detecting part. A target substance is captured by the primary capturing body and, consequently, a magnetic label is immobilized in the vicinity of the detecting part and the detecting part recognizes the magnetic label. Thus, the detection of the target substance is carried out by utilizing a change in the signal due to the presence of the magnetic label.

In the present invention, the detecting part of the detecting element refers to a part having a function measuring the presence or amount of the target substance in a sample solution based on the presence or amount of the magnetic label. The detecting part provided with a primary capturing body for capturing the target substance on the surface thereof. The non-detecting part refers to a part other than the detecting part in the detecting element. As long as the non-detecting part and the detecting part of the detecting element are adjacent to each other, they may be partially in contact with each other or the none detection may be disposed so as to surround the detecting part.

If the surface potentials of the detecting part and the non-potential part with respect to the surface potential of the magnetic label satisfy any one of the relationships i) to iv) when a primary capturing body of the detecting part captures the target substance borne by the magnetic label or a secondary capturing body of the magnetic label captures the target substance captured by a primary capturing body of the detecting part, the detecting part and the non-detecting part may be constituted with one layer or may be a layered structure of a plurality of layers. The surface potential of the detecting part or the non-detecting part may be controlled by the property of the material forming the surface of the detecting part or the non-detecting part or may be controlled by applying a voltage or current to one of the detecting part and the non-detecting part or both by connecting to an external power supply. In such a case, the detecting part or the non-detecting part has a terminal for applying a voltage or current by an external power supply.

When the surface potential is controlled by the material forming the surface of the detecting part or the non-detecting part and the detecting part or the non-detecting part is formed into one layer, a material whose surface potential satisfies the above-mentioned conditions is preferably used as the substrate. Further, the detecting part and the non-detecting parts are formed into one layer, the detecting part and the non-detecting part are formed of different materials. On the other hand, when the surface potential is controlled by the material forming the surface of the detecting part or the non-detecting part and the detecting part or the non-detecting part is a layered structure of a plurality of layers, a material whose surface potential satisfies the above-mentioned conditions is preferably used as the outermost layer. Examples of the material which satisfies the above-mentioned conditions include a polymer containing a functional group which becomes an anion or a functional group which becomes a cation and an inorganic oxide having an isoelectric point in a solution at a specific temperature or pH. An example of the functional group which becomes an anion in a solution at a specific temperature or pH is a carboxyl group, and an example which becomes a cation is an amino group. In addition, as long as the surface potential of the outermost layer of a layered structure satisfies the above-mentioned conditions, layers other than the outermost layer may be formed of a material not having a surface potential or a material having a surface potential which does not satisfy the above-mentioned conditions. Further, when the material forming the outermost layer does not satisfy the above-mentioned conditions as a single material, the outermost layer may be formed of such a material as long as the layered structure satisfies the above-mentioned conditions.

Figure 7:
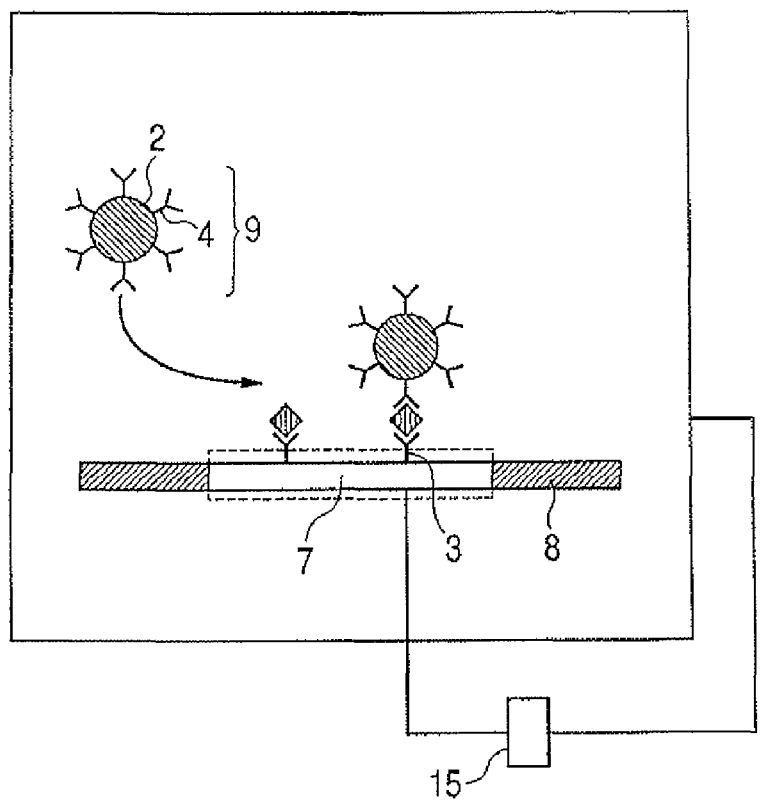
FIG. 7 is a schematic diagram illustrating a detecting element according to an embodiment in which the polarity of the surface potential of a detecting part can be controlled by applying a voltage or current.

Further, when the surface potential is controlled by applying a voltage or current by connecting the detecting part or the non-detecting part to an external power supply, a material not having a surface potential or having a surface potential which does not satisfy the above-mentioned conditions when the external power supply is not connected may be used as long as the surface potential can be controlled to the above-mentioned conditions by applying the surface potential to the detecting part or the non-detecting part by the external power supply. FIG. 7 illustrates an embodiment in which the detecting part is connected to an external power supply. In this embodiment, a potential is added to the surface of the detecting part by the external power supply 15. In this method, preferably, the surface potential of the detecting part 7 can be readily altered according to the surface potential of the magnetic label.

Further, preferably, a molecule having an active group is previously immobilized on a part of the substrate surface serving as a part of the detecting part, and a primary capturing body serving as another part of the detecting part is immobilized via the active group.

(Capturing Body)

The capturing body used in the present invention is a material which is involved in the selection of a target substance in a sample solution and can be selected according to the target substance.

Here, the target substance in the present invention will be described in advance of the description of the capturing body in the present invention.

The target substance is contained in a sample solution which is reacted with a detecting element. The target substance is captured at least by a primary capturing body on the surface of a detecting part. The target substance in the present invention is typically a chemical material (biological material) present in the body of an organism. In the present invention, generally, the object to be detected itself is the target substance.

Actually, in the present invention, an object to be detected may be detected by using a target substance. Therefore, the object to be detected itself is the target substance as described above and may be directly detected by capturing the object by a capturing body, or the object to be detected is different from the target substance and may be indirectly detected by capturing the target substance by a capturing body. An example of the latter is a case that a target substance is generated by the presence of an object to be detected. Therefore, the object to be detected is not limited to biological materials and the size of the object is not limited. However, preferable examples of the target substance are biological materials such as sugars, proteins, amino acids, antibodies, antigens, pseudo-antigens, vitamins, genes, related materials thereof, and artificially synthesized biomimetic materials. In addition, the sample solution may be a specimen itself containing an object to be determined or may be prepared by treating a specimen by various processes such as extraction, separation, dilution, or purification. The sample solution is prepared by using a liquid solvent, such as water, buffer, or mixture of water and a water-soluble organic solvent, depending on the type of a target substance.

The capturing bodies used in the present invention are materials which can capture the above-mentioned target substances referred to as examples, examples of which include proteins such as enzymes, antibodies, and antigens; DNAS; RNAs; and sugar chains, but not limited thereto.

Examples of a combination of a target substance and a primary or secondary capturing body in the present invention include antigen-antibody, enzyme-substrate, DNA-DNA, DNA-RNA, DNA-protein, RNA-protein, and sugar chain-protein, but not specifically limited thereto as long as the combination is in a specific binding. The above shows the combination. Therefore, when a combination of a target substance and a capturing body is expressed as "A-B", it means both cases that the A denotes a target substance and the B denotes a capturing body and that the B denotes a target substance and the A denotes a capturing body.

<Target-Substance Detection Kit>

The target-substance detection kit according to this embodiment includes a magnetic label and a target-substance detecting element. The target-substance detecting element consists of the above-described target-substance detecting element.

(Magnetic Label)

A magnetic label used in the present invention includes at least a magnetic structure and a secondary capturing body for capturing a target substance on the surface of the magnetic structure, or a complex of a secondary target substance and target substance. That is, there are cases that the magnetic label includes a magnetic structure and a secondary capturing body on the surface of the magnetic structure and that the magnetic label includes a magnetic structure, a secondary capturing body on the surface of the magnetic structure, and a target substance captured by the secondary capturing body. The magnetic label is required to have a surface potential when the target substance borne by the magnetic label is captured by a primary capturing body of a detecting part or when the secondary capturing body borne by the magnetic label captures a target substance captured by a primary capturing body borne by a detecting part. Furthermore, the magnetic label is required to satisfy physical properties or characteristics as a label for detecting a target substance. Therefore, the magnetic structure may be selected from generally used fine magnetic particles (magnetic beads) exhibiting paramagnetism or superparamagnetism.

Examples of a magnetic material constituting the magnetic structure include metal oxides. Metal oxides are readily charged in an aqueous solution, namely, are positively charged at a pH lower than the isoelectric point and are negatively charged at a pH higher than the isoelectric point and, therefore, are preferable. Among metal oxides, particularly, particles of iron oxides such as ferrite and magnetite which are generally used as magnetic structures of magnetic labels exhibit sufficient magnetism under bioactive conditions and are negligibly degraded, such as oxidation, in a solvent. Therefore, iron oxide particles are preferable. Ferrite is selected from magnetite ($Fe_3O_4$), maghemite ($\gamma$-$Fe_2O_3$), and complexes thereof obtained by substituting a part of Fe with another atom. Examples of the another atom include Li, Mg, Al, Si, Ca, Sc, Ti, V, Cr, Mn, Co, Ni, Cu, Zn, Ga, Ge, Zr, Nb, Mo, Cd, In, Sn, Ta, and W.

The magnetic structure may be core-shell particles which are formed by using a substrate consisting of a magnetic material as a core and forming a polymer layer (resin layer) on the surface of the substrate for improving dispersibility. The resin layer may be formed, for example, of a styrene-based, dextran-based, or acrylamide-based resin. Here, the styrene-based resin is defined as a resin consisting of styrene and styrene derivatives. The dextran-based resin and the acrylamide-based resin are similarly defined. In addition, a resin obtained by copolymerizing at least two monomers forming a styrene-based resin, a dextran-based resin, or an acrylamide-based resin is also contained in a styrene-based, dextran-based, or acrylamide-based resin.

When a resin layer formed as described above has a surface potential in a sample solution and thereby the magnetic label has a surface potential, a layered structure composed of a metal oxide and a resin layer can be used in a magnetic label as the magnetic structure.

Further, when the resin layer does not have a sufficient surface potential in a sample solution, a layered structure prepared by using the coreshell particle as a substrate and further forming a coating layer described below on the surface of the substrate may be used. In addition, besides the core-shell type particles, particles prepared by dispersing fine particles composed of a magnetic material in a styrene-based, dextran-based, or acrylamide-based resin or particles supporting fine particles composed of a magnetic material on the surfaces of resin particles may be used as the magnetic structure of the present invention. As these magnetic structures, for example, Dynabeads is commercially available from Dynal, Micromer-M and Nanomag-D are commercially available from Micromod, and Estapor is commercially available from Merk.

The size of the magnetic structure may variously vary depending on the shape, size, or use of a detecting element. In general, the diameter of a magnetic structure is preferably 3 nm to 500 μm, more preferably 3 nm to 10 μm, and further preferably 5 nm to 1 μm. The diameter or average particle size of the magnetic structure can be measured by a dynamic light scattering method.

The magnetic label is preferably provided with a secondary capturing body for capturing a target substance on the surface of the magnetic structure. Further, preferably, a primary capturing body of a detecting part specifically recognizes a primary region of a target substance in a sample solution and captures the target substance through the primary region, and the secondary capturing body of the magnetic label specifically recognizes a secondary region of the target substance in the sample solution and captures the target substance through the secondary region. Here, the secondary region is different from the primary region and is at least an area of a region other than the primary region of the target substance. In this case, both the magnetic label and the detecting part each have a capturing body on the surface thereof, and the target substance is captured by both the primary capturing body on the surface of the magnetic label and the secondary capturing body on the surface of the detecting part. Consequently, the magnetic label is immobilized in the vicinity of the surface of the detecting part via the target substance. The detecting part detects the immobilized magnetic label and the target substance can be readily detected.

Further, when a magnetic label is provided with a target substance on the surface thereof, the target substance can be detected by capturing the target substance by a capturing body on the surface of a detecting part even if the magnetic label is not provided with a secondary capturing body on the surface. In such a case, the target substance on the surface of the magnetic label preferably includes at least two regions, i.e., a region where the target substance is immobilized to the magnetic label and a region where the target substance is captured by the primary capturing body on the surface of the detecting part. Further, when a magnetic label includes a complex of a target substance and a secondary capturing body, the target substance can be detected by capturing the target substance by a primary capturing body borne by a detecting part. In this specification and the present invention, the concept that a magnetic label is provided with a target substance on the surface of a magnetic structure includes a case that a magnetic label is provided with a complex of a target substance and a secondary capturing body as a result that the secondary capturing body has captured the target substance.

The above-described detecting element and the magnetic label can constitute a target-substance detection kit. That is, the kit can be used for detecting the presence or concentration of a target substance in a sample solution by bringing the sample solution into contact with the surface of a detecting part of the detecting element to lead the target substance to the detecting part and detecting the presence or number of the magnetic label present in the vicinity of the surface of the detecting part.

(Coating Layer)

The magnetic label and the detecting element according to the present invention may each have a layered structure composed of a plurality of layers, as described above. The layered structure composed of a plurality of layers can be prepared, for example, by forming at least one layer on the surface of a substrate. In such a case, the outermost layer of the layered structure composed of a plurality of layers containing the substrate is called a coating layer. Therefore, when one layer is formed on the surface of a substrate, the layer is a coating layer. In the present invention, a substrate or a magnetic structure in a state before the formation of a coating layer or a resin layer is called a substrate for the convenience of description.

The surface potential of the substrate surface can be controlled by forming a coating layer. Therefore, the relationships i) to iv) can be satisfied by forming a coating layer on any one of the surfaces of the magnetic label, the detecting part, and the non-detecting part even if the magnetic label, the detecting part, and the non-detecting part do not satisfy any of the relationships i) to iv). Even if the substrates of the magnetic label and the detecting element are composed of a material which exhibits a zero or near-zero surface potential in a sample solution, the effect of the present invention can be obtained. Any materials can be used as a coating layer as long as the material can exhibit a surface potential in a sample solution according to purpose. A material selected from, for example, inorganic materials such as glass, organic materials such as resins, semiconducting materials such as silicon, and metal materials can be used according to purpose.

Further, when the target substance or the capturing body is a biological material, these coating layers are preferably a hydrophilic layer.

Generally, biological materials such as proteins are hydrophobic. Therefore, when the coating layer is hydrophobic, non-specific adsorption to the coating layer is readily caused by "hydrophobic interaction".

For example, if a target substance is non-specifically adsorbed to the surface of a detecting part at a region other than a primary capturing body, a secondary capturing body on the surface of a magnetic label captures the non-specifically adsorbed target substance and thereby the signal of the magnetic label occurs as a noise. This noise may cause a decrease in the detection sensitivity or accuracy. In addition, when a secondary capturing body borne by the surface of a magnetic label or a target substance borne by the surface of a magnetic label is non-specifically adsorbed directly to a non-detecting part or a detecting part without the presence of a target substance, a decrease in the detection sensitivity or accuracy may be similarly caused.

On the other hand, when the coating layer is hydrophilic, "hydrophobic interaction", which is one cause of non-specific adsorption of biological materials, can be reduced. Thus, non-specific adsorption of biological materials can be decreased. The hydrophilic coating layer is formed of, for example, a graft polymer such as polyglycidyl methacrylate, PHEMA (poly(2-hydroxyethyl methacrylate)), or polyethylene glycol methacrylate. Among them, polyglycidyl methacrylate is excellent in the prevention of non-specific adsorption of biological materials such as proteins. Further, a functional group such as an amino group can be introduced into polyglycidyl methacrylate by opening the epoxy group. Therefore, polyglycidyl methacrylate is preferable as a material of the coating layer allowing a substrate surface to have a surface potential.

(Detection Method)

In a detection system according to the present invention, the presence or concentration of a target substance in a sample solution is determined by detecting the presence or number of a magnetic label present in the vicinity of the surface of a detecting part. For determining the target-substance concentration in a sample solution, preferably, the number of a magnetic label present in the vicinity of a detecting part is determined and the target-substance concentration is determined base on a calibration curve previously prepared. Examples of the detection methods will be described below.

(First Case)

A primary capturing body is immobilized on the surface of a detecting part. Then, a sample solution containing a target substance is brought into contact with the detecting part. On this occasion, if the sample solution contains a desired target substance, the primary capturing body captures the target substance. The sample solution is washed out from the surface of the detecting part to remove unwanted materials. Then, a solution containing a magnetic label provided with a secondary capturing body for capturing the target substance on the surface thereof is brought into contact with the washed surface of the detecting part of the detecting element (refer to FIG. 2 mentioned above).

Then, the surface of the detecting part is washed to remove the magnetic label not bound to the detecting part. After that, the target substance can be indirectly detected by detecting the magnetic label. Furthermore, when the target substance captured by the primary capturing body on the surface of the detecting part is further captured by the secondary capturing body of the magnetic label, the surface potential of the magnetic label and the surface potential of the detecting element are controlled to satisfy the above-described characteristic in the relationship therebetween.

As an example of such a system, a case that the target substance is an antigen, the primary capturing body is a primary antibody, and the secondary capturing body is a secondary antibody is cited. In this case, the capture of the target substance by the primary capturing body is an antigen-antibody reaction. Further, the secondary antibody here is an antibody which captures the antigen captured by the primary antibody at a region other than the region of the antigen where the primary antibody captured. The primary antibody and the secondary antibody may be the same type or different type. In addition, the antigen region captured by the primary antibody and the antigen region captured by the secondary antibody may be different epitopes or the same epitope.

(Second Case)

As in the First Case, a primary capturing body is immobilized on the surface of a detecting part. Then, a target substance is immobilized to the surface of a magnetic label. A sample solution containing the magnetic label immobilizing the target substance is brought into contact with the surface of the detecting part. The surface of the detecting part is washed to remove the magnetic label not bound to the detecting part. Then, the target substance is indirectly detected by detecting the magnetic label (refer to FIG. 3 mentioned above).

Furthermore, when the target substance borne by the magnetic label is captured by the primary capturing body borne by the surface of the detecting part, the surface potential of the magnetic label and the surface potential of the detecting element are controlled to satisfy the above-described characteristic in the relationship therebetween.

As examples of such a system, cases that the target substance is an antigen and the primary capturing body is an antibody and that the target substance is an antibody and the primary capturing body is an antigen are cited.

(Third Case)

A secondary capturing body is immobilized on the surface of a magnetic label, and then a target substance is captured by the secondary capturing body. Then, as in the First Case, a primary capturing body is immobilized on the surface of a detecting part. A sample solution containing the magnetic label provided with a complex of the target substance and the secondary capturing body on the surface thereof is brought into contact with the surface of the detecting part so that the target substance captured by the secondary capturing body is captured by the primary capturing body. Then, the surface of the detecting part is washed to remove the magnetic label not bound to the detecting part. The target substance can be indirectly detected by detecting the magnetic label (refer to FIG. 4 mentioned above).

Furthermore, when the target substance captured by the secondary capturing body borne by the surface of the magnetic label is further captured by the primary capturing body borne by the surface of the detecting part, the surface potential of the magnetic label and the surface potential of the detecting element are controlled to satisfy the above-described characteristic in the relationship therebetween.

Here, in the present invention, the state in that the secondary capturing body borne by the surface of the magnetic label is capturing the target substance is defined that the magnetic label is provided with the secondary capturing body and the target substance on the surface thereof and is included in the concept of "magnetic label is provided with a target substance".

Further, just after the contact of a sample solution with a detecting part, a solution containing a magnetic label provided with a secondary capturing body may be brought into contact with the detecting part, or both may be carried out simultaneously. In such a case, it is thought that both reactions in the First Case and the Third Case occur. Therefore, when the target substance on the magnetic label is captured by the primary capturing body of the detecting part and when the target substance captured by the primary capturing body of the detecting part is captured by the secondary capturing body of the magnetic label, the surface potential of the magnetic label and the surface potential of the detecting element are controlled to satisfy the above-described characteristic in the relationship therebetween. Since the term "OR" means a concept including "AND", the above-mentioned case is within the scope of the present invention.

In the First to Third Cases, any detection methods can be used as long as a magnetic label present in the vicinity of the surface of a detecting part is detected. In particular, a method using a magnetic-field effect caused by the magnetic label present at the surface of the detecting part is preferable. Specifically, a magnetoresistive element, a hall effect element, or a superconducting quantum interference device can be suitably used.

The relationships among the surface potentials of a magnetic label, a detecting part, and a non-detecting part will be described with reference to First to Fourth Embodiments.

First Embodiment

In this Embodiment, the surface potential $\psi_1$ of a magnetic label, the surface potential $\psi_2$ of a detecting part, and the surface potential $\psi_3$ of a non-detecting part are in the relationship i); and a target substance on the magnetic label is captured by a primary capturing body of the detecting part, or a target substance captured by a primary capturing body of the detecting part is captured by a secondary capturing body of the magnetic label, $$\psi_1\psi_3>0 \text{ and } \psi_2=0. \qquad \text{i)}$$

The $\psi_1$, $\psi_2$, and $\psi_3$ satisfying this relationship are as follows:

$$\psi_1<0, \psi_2=0 \text{ and } \psi_3<0, \text{ or} \qquad \text{I)}$$

$$\psi_1>0, \psi_2=0, \text{ and } \psi_3>0. \qquad \text{II)}$$

In this embodiment, since the surface potential $\psi_1$ of the magnetic label and the surface potential $\psi_3$ of the non-detecting part have the same polarity, a repulsive force (electrostatic repulsive force) is generated between the magnetic label and the non-detecting part. In addition, the detecting part does not exhibit a polarity. Therefore, the magnetic label is indirectly led to the detecting part by the repulsive force between the $\psi_1$ and $\psi_3$. Consequently, the non-specific adsorption of the magnetic label to the non-detecting part is decreased (a reduction in noise) and the detection of the target substance can be carried out with high sensitivity and high accuracy.

Second Embodiment

In this Embodiment, the surface potential $\psi_1$ of a magnetic label, the surface potential $\psi_2$ of a detecting part, and the surface potential $\psi_3$ of a non-detecting part are in the relationship ii); and a target substance borne by the magnetic label is captured by a primary capturing body borne by the detecting part, or a target substance captured by a primary capturing body borne by the detecting part is captured by a secondary capturing body borne by the magnetic label, $$\psi_1\psi_2<0 \text{ and } \psi_3=0. \qquad \text{ii)}$$

The $\psi_1$, $\psi_2$, and $\psi_3$ satisfying this relationship are as follows:

$$\psi_1<0, \psi_2>0, \text{ and } \psi_3=0, \qquad \text{or III)}$$

$$\psi_1>0, \psi_2<0, \text{ and } \psi_3=0. \qquad \text{IV)}$$

In this embodiment, since the surface potential $\psi_1$ of the magnetic label and the surface potential $\psi_2$ of the detecting part have opposite polarities, an electrostatic attractive force is generated between the magnetic label and the detecting part. On the other hand, since the non-detecting part does not have a charge, an electrostatic attractive force is not generated between the magnetic label and the non-detecting part. Therefore, the magnetic label is led to the detecting part by the electrostatic attractive force between the $\psi_1$ and $\psi_2$. Consequently, the non-specific adsorption of the magnetic label to the non-detecting part is decreased and the magnetic label is rapidly and selectively led to the detecting part. As a result, the detection of the target substance can be carried out with high sensitivity and high accuracy.

Third Embodiment

In this Embodiment, the surface potential $\psi_1$ of a magnetic label, the surface potential $\psi_2$ of a detecting part, and the surface potential $\psi_3$ of a non-detecting part are in the relationship iii); and a target substance borne by the magnetic label is captured by a primary capturing body borne by the detecting part, or a target substance captured by a primary capturing body borne by the detecting part is captured by a secondary capturing body borne by the magnetic label, $$\psi_1\psi_2<0, \psi_2\psi_3>0, \text{ and } |\psi_2|>|\psi_3|. \qquad \text{iii)}$$

The $\psi_1$, $\psi_2$, and $\psi_3$ satisfying this relationship are as follows:

$$\psi_1>0 \text{ and } \psi_2<\psi_3<0, \text{ or} \qquad \text{V)}$$

$$\psi_1<0 \text{ and } \psi_2>\psi_3>0. \qquad \text{VI)}$$

In this embodiment, since the surface potential $\psi_1$ of the magnetic label and the surface potential $\psi_2$ of the detecting part have opposite polarities, an electrostatic attractive force is generated between the magnetic label and the detecting part. In addition, since the surface potential $\psi_1$ of the magnetic label and the surface potential $\psi_3$ of the non-detecting part also have opposite polarities, an electrostatic attractive force is generated between the magnetic label and the non-detecting part. However, there is a relationship of $|\psi_2|>|\psi_3|$, so that the electrostatic attractive force generated between the magnetic label and the detecting part is greater than that between the magnetic label and the non-detecting part. Therefore, the magnetic label is rapidly and selectively led to the detecting part, and the detection of the target substance can be carried out with high sensitivity and high accuracy.

Fourth Embodiment

In this Embodiment, the surface potential $\psi_1$ of a magnetic label, the surface potential $\psi_2$ of a detecting part, and the surface potential $\psi_3$ of a non-detecting part are in the relationship iv); and a target substance borne by the magnetic label is captured by a primary capturing body borne by the detecting part, or a target substance captured by a primary capturing body borne by the detecting part is captured by a secondary capturing body borne by the magnetic label, $$\psi_1\psi_2<0 \text{ and } \psi_2\psi_3<0. \qquad \text{iv)}$$

The $\psi_1$, $\psi_2$, and $\psi_3$ satisfying this relationship are as follows:

$$\psi_1>0, \psi_2<0, \text{ and } \psi_3>0, \text{ or} \qquad \text{VII)}$$

$$\psi_1<0, \psi_2>0, \text{ and } \psi_3<0. \qquad \text{VIII)}$$

In this embodiment, since the surface potential $\psi_1$ of the magnetic label and the surface potential $\psi_2$ of the detecting part have opposite polarities, an electrostatic attractive force is generated between the magnetic label and the detecting part. On the other hand, since the surface potential $\psi_1$ of the magnetic label and the surface potential $\psi_3$ of the non-detecting part have the same polarity, a repulsive force is generated between the magnetic label and the non-detecting part. Consequently, the non-specific adsorption of the magnetic label to the non-detecting part is decreased and the magnetic label is rapidly and selectively led to the detecting part. As a result, the detection of the target substance can be carried out with high sensitivity and high accuracy.

In this Embodiment, it is preferable that the non-detecting part and the magnetic label each have a layered structure and that the outermost layer of the non-detecting part and the outermost layer (coating layer) of a magnetic structure be formed of the same material. The magnetic structure is a magnetic label before the immobilization of a capturing body or a target substance. By forming the coating layers on the surfaces of the non-detecting part and the magnetic structure with the same material, the polarity of the surface potential of the magnetic label and the polarity of the surface potential of the non-detecting part in a sample solution can be readily controlled to be the same. That is, the repulsive force can be readily generated between the magnetic label and the non-detecting part. FIG. 6 shows a detecting element including a non-detecting part 8 having a coating layer 16 and a detecting part 7 and a magnetic label having a coating layer 16.

The coating layer 16 is preferably formed of a graft polymer, which can be formed by living radical polymerization. The living radical polymerization can precisely control the molecular weight, molecular weight distribution (weight average molecular weight/number average molecular weight), and graft density of the graft polymer. By precisely controlling the graft density of the graft polymer present in the surfaces of the non-detecting part and the magnetic structure, the surfaces of the non-detecting part and the magnetic label can be controlled to the same polarity and the non-specific adsorption of the magnetic label to the non-detecting part can be prevented. More preferably, the surfaces of the non-detecting part and the magnetic label have the same polarity and the absolute values of the surface zeta potentials of the non-detecting part and the magnetic label are large. Examples of the graft polymer include polyglycidyl methacrylate, PHEMA, and polyethylene glycol methacrylate.

A method for forming a graft polymer will be described below. The formation of a graft polymer on a substrate can be carried out by at least the processes 1) and 2) below. Here, the substrate is a non-detecting part or a magnetic structure before the formation of a graft polymer, and the substrate surface is the surface of the non-detecting part or the surface of the magnetic structure before the formation of a graft polymer.

1) Process for introducing a living polymerization initiator group to the surface of a substrate, and
2) Process for conducting living polymerization of a monomer from the living polymerization initiator group to form a graft polymer binding to the living polymerization initiator group.

Generally, the living radical polymerization can freely select the type of monomer, the degree of polymerization, and the formation of copolymer. Therefore, the molecular weight, molecular weight distribution, and graft density of the graft polymer on the substrate surface can be precisely controlled. Examples of the living polymerization include living radical polymerization, living cation polymerization, and living anion polymerization. Among them, the living radical polymerization is preferable because of its simplicity of polymerization. As the living radical polymerization, atom transfer radical polymerization, nitroxide mediated polymerization, reversible addition fragmentation chain transfer (RAFT) polymerization, or photoinitiated polymerization can be used. Here, a method using the atom transfer radical polymerization will be specifically described in detail.

Regarding the Process 1)

A method for introducing an atom transfer radical polymerization initiator group to a substrate will be described.

An atom transfer radical polymerization initiator group can be introduced to the surface of a substrate by reacting a functional group present in the surface of the substrate to a functional group of a precursor of the atom transfer radical polymerization initiator group. For example, the reaction can be carried out according to the following reaction formula (I):

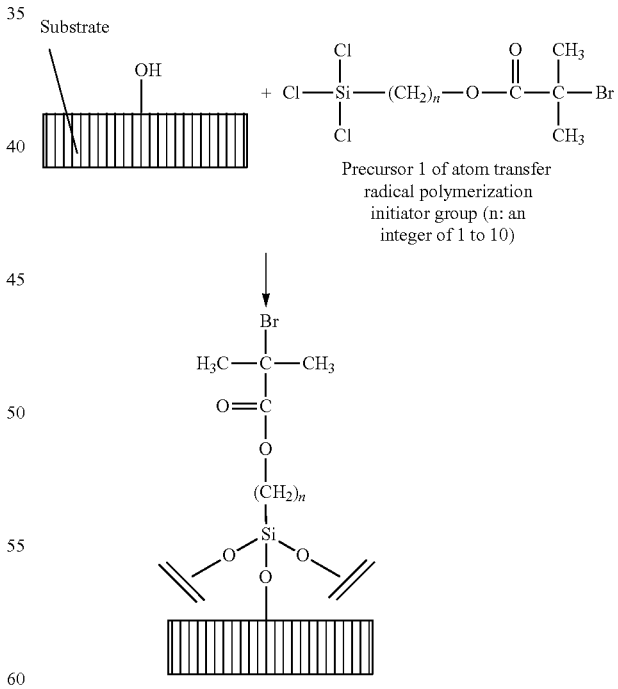

That is, a substrate is immersed in a reaction solvent, and then precursor 1 of an atom transfer radical polymerization initiator group is added thereto under an inert gas atmosphere to react a hydroxyl group of the substrate surface with a trichlorosilyl group of precursor 1 of the atom transfer radical polymerization initiator group. With this, the atom transfer radical polymerization initiator group can be introduced to the substrate surface. The functional group of precursor 1 of the atom transfer radical polymerization initiator group may be a trimethoxysilyl group or triethoxysilyl group instead of the trichlorosilyl group.

As the inert gas, nitrogen gas or argon gas can be used. The reaction solvent is not specifically limited, and examples of which include dimethylsulfoxide, dimethylformamide, tetrahydrofuran, benzene, toluene, and xylene.

Instead of precursor 1 of the atom transfer radical polymerization initiator group, precursors 2 to 4 of the atom transfer radical polymerization initiator group described below may be used. Further, a trimethoxysilyl group or triethoxysilyl group may be used instead of the trichlorosilyl group of precursors 2 to 4 of the atom transfer radical polymerization initiator group.

Precursor 2 of Atom Transfer Radical Polymerization Initiator group;

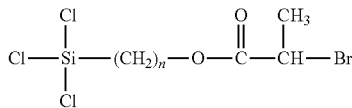

(n: an integer of 1 to 10)
Precursor 3 of Atom Transfer Radical Polymerization Initiator Group:

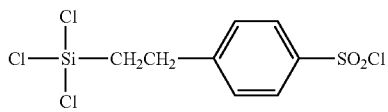

Precursor 4 of Atom Transfer Radical Polymerization Initiator Group:

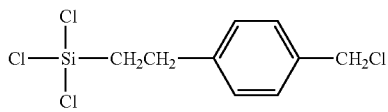

The reaction temperature is not specifically limited as long as the above-mentioned reaction is performed, but is preferably in a range of from 0 up to 100° C. The concentration of the precursor of an atom transfer radical polymerization initiator group is preferably in a range of 1 to 5 equivalents to the concentration of the functional group of a substrate surface.

The number of the introduced living polymerization initiator group is optionally adjusted to an intended graft density. For example, a living polymerization initiator group can be introduced to a substrate surface at a graft density of from 0.01 molecules/nm$^2$ or more and 1.0 molecules/nm$^2$ or less. In addition, when a magnetic structure is fine magnetic particles on which a graft polymer is formed, the average diameter of the fine magnetic particles on which the graft polymer is formed is preferably 3 nm or more and 500 μm or less, more preferably from 5 nm or more and 1 μm or less.

Regarding to the Process 2)
(Living Polymerization)

Next, atom transfer radical polymerization will be described. In the atom transfer radical polymerization, for example, if a copper halide-bipyridyl complex is used, a polymer having a narrow molecular weight distribution can be obtained by rapid transfer reaction of the polymer chain end. In this atom transfer radical polymerization, the reaction is performed by reversely drawing a halogen atom from the growing end with the copper complex. Factors for controlling the reaction in the atom transfer radical polymerization include the types of ligand and initiator group, catalyst concentration, reaction temperature, reaction time, and concentration. A polymer having a narrow molecular weight distribution can be formed by optimizing these conditions and controlling the reaction. Therefore, a graft polymer having a uniform chain length can be readily formed by conducting the atom transfer radical polymerization to the substrate to which an atom transfer radical polymerization initiator group is introduced.

Specifically, a substrate is immersed in a reaction solvent, and a monomer which becomes a graft polymer and a transition metal complex are added thereto to conduct an atom transfer radical polymerization by purging the reaction system with an inert gas. Thus, the polymerization can be performed while maintaining a constant graft density of a graft polymer. That is, all graft polymers can be substantially uniformly grown on the surface of the substrate by livingly polymerizing graft polymers.

Any reaction solvent can be used as long as living polymerization can be performed. The solvent may be used alone or as a combination of two or more.

The inert gas may be nitrogen gas or argon gas.

The transition metal complex may be a complex consisting of a metal halide and a ligand. The metal of the metal halide is preferably selected from transition metal elements from Ti of atomic number 22 to Zn of atomic number 30 and is more preferably Fe, Co, Ni, or Cu. Among them, cuprous chloride and cuprous bromide are most preferable.

The ligand is not specifically limited as long as coordinate bond with a metal halide is possible. Examples of the ligand include 2,2'-bipyridyl, 4,4'-di-(n-heptyl)-2,2'-bipyridyl, 2-(N-pentyliminomethyl)pyridine, (−)-sparteine, tris(2-dimethylaminoethyl)amine, ethylene diamine, dimethylglyoxime, 1,4,8,11-tetramethyl-1,4,8,11-tetraazacyclotetradecane, 1,10-phenanthroline, N,N,N',N'',N''-pentamethyldiethylene triamine, and hexamethyl(2-aminoethyl)amine.

The transition metal complex is added to a monomer which becomes a graft polymer at a ratio of preferably 0.001 mass % or more and 10 mass % or less, more preferably 0.05 mas % or more and 5 mass % or less.

The polymerization temperature is preferably in a range of from 40° C. up to 100° C., more preferably a range of from 50° C. up to 80° C.

In addition, on the occasion of the polymerization, a free polymerization initiator which is not immobilized to a substrate is preferably added. The free polymer generated from this free polymerization initiator can be used as an indicator of the molecular weight and the molecular weight distribution of a graft polymer formed on the substrate surface.

The free polymerization initiator is preferably the same type as the atom transfer radical polymerization group immobilized on the substrate. That is, when a polymerization initiator group is introduced to a substrate by precursor 1 of an atom transfer radical polymerization initiator group, a preferable free polymerization initiator is ethyl 2-bromoisobutyrate. When a polymerization initiator group is introduced to a substrate by precursor 2 of an atom transfer radical polymerization initiator group, a preferable free polymerization initiator is ethyl 2-bromopropionate. When a polymerization initiator group is introduced to a substrate by precursor 3 of an atom transfer radical polymerization initiator group, a preferable free polymerization initiator is benzenesulfonyl chloride. When a polymerization initiator group is introduced to a substrate by precursor 4 of an atom transfer radical polymerization initiator group, a preferable free polymerization initiator is benzyl chloride.

(Graft Polymer)

The graft polymer which is formed on a substrate will be described. The graft polymer which is formed on a substrate can be formed by livingly polymerizing a monomer in the presence of the substrate having an introduced living polymerization initiator group. The graft polymer on this occasion is bound to the living polymerization initiator group and is a non-cross-linked polymer chain grown into a straight-chain. The graft density of the graft polymer formed on a substrate is preferably in a range of 0.01 to 1 molecules/nm$^2$. The graft density corresponds to a density of a living polymerization initiator group on the substrate surface where the graft polymer is formed and can be controlled by the introduction ratio of the living radical polymerization initiator group.

The graft density of a graft polymer can be determined from the film thickness and the weight of the graft polymer formed on a substrate. The thickness of a graft polymer formed on a substrate can be determined by spectroscopic ellipsometry, and the weight of a graft polymer can be determined with a precise weight scale from a difference in the weight of a substrate before and after the living polymerization. In such a case, the values are preferably determined using a detecting element.

The graft polymer formed on the substrate surface is preferably a hydrophilic polymer. Here, in the present invention, the term "hydrophilic" means that the contact angle with water is in a range of 0 to 90 degrees. The graft polymer has an affinity to water and is elongated thereby in a water-soluble sample solution. Furthermore, if the graft density of a graft polymer becomes higher, the polymer has a structure standing perpendicular to the substrate, like a brush. With such a structure, the blocking effect of the graft polymer is also increased, in addition to the repulsive force generated by that the magnetic label and the non-detecting part have the same polarity. Examples of the blocking polymer include 2-hydroxyethyl acrylate polymers, 2-hydroxyethyl methacrylate polymers, acrylamide polymers, methacrylamide polymers, polyethylene glycol acrylate polymers, methoxypolyethylene glycol acrylate polymers, polyethylene glycol methacrylate polymers, and methoxypolyethylene glycol methacrylate polymers. These polymers may be used alone or as a combination of two or more thereof.

The monomer for forming these graft polymers is used at an amount necessary for forming a graft polymer having a desired number average molecular weight. For example, a monomer of from 5 molecules or more and 10000 molecules or less to one living polymerization initiator group can be used.

The number average molecular weight of a graft polymer is preferably in a range of from 500 up to 1,000,000, more preferably from 1,000 up to 500,000. When the number average molecular weight of a graft polymer is lower than 500, the blocking effect may be insufficient. On the other hand, when the number average molecular weight of a graft polymer is higher than 1,000,000, the solubility to water may be decreased.

Further, it is preferable that the molecular weight distribution of a graft polymer formed on a substrate surface be narrow for suppressing a variation in the surface potential of the non-detecting part or the magnetic label. The molecular weight distribution (weight average molecular weight/number average molecular weight) of a graft polymer is preferably a 1.8 or less, more preferably 1.5 or less.

In addition, the number average molecular weight and the molecular weight distribution of a graft polymer formed on a substrate surface can be estimated to be the same as those of a free polymer generated from a free polymerization initiator as described above. The number average molecular weight and the molecular weight distribution of a graft polymer can be measured with GPC (AS-8020 manufactured by Toso, eluent: water, standard polymer: polyethylene oxide). In addition, the chain length (number average molecular weight) and the molecular weight distribution of a graft polymer can be controlled by adjusting the amount of monomer, polymerization time or the like.

Further, the immobilization of a capturing body (secondary capturing body) for capturing a target substance or the immobilization of a target substance to a magnetic structure having a graft polymer on the surface thereof can be carried out by the following processes. Here, for simplifying the description, an example for immobilizing a secondary capturing body on a magnetic structure surface will be described, but a target substance can be immobilized to a magnetic structure by the same manner.

Process for introducing an active group to ends of parts of the graft polymer, and Process for binding a secondary capturing body to the introduced active group.

The respective processes will be described in detail.

(Introduction of Active Group into the End of Graft Polymer)

Any active group may be introduced to a graft polymer as long as the group can be bound to a secondary capturing body. Examples of the active group include a carboxyl group and an amino group which can bind with a protein by an amide bond. Here, the term "active group" means a functional group which can react with a functional group of a secondary capturing body. The introduction of an active group to an end of a polymer chain can be carried out, for example, by a method for adding a chain transfer agent during a process of polymerizing a graft polymer. The chain transfer agent is a material which transfers the active site, generally, in radical polymerization reaction by a chain transfer reaction. The chain transfer agent is used for converting a polymer end to a desired functional group.

A preferable chain transfer agent is a thiol compound. As a thiol compound which is effective as a chain transfer agent, one having a thiol group at one end of an alkyl chain having two or more carbon atoms and a desired functional group at the other end is used. The desired functional group is one for immobilizing a secondary capturing body, namely, an active group. Examples of the active group include a carboxyl group, an active ester group, and an amino group. Examples of the chain transfer agent having an active group include a mercaptoacetic acid.

Further, the amount of an active group introduced to an end of a polymer chain can be controlled by adding both a chain transfer agent having the active group and a chain transfer agent having an inactive group at a desired ratio. A preferable chain transfer agent having an inactive group is a compound having a thiol group at one end of an alkyl chain having two or more carbon atoms and a hydroxyl group at the other end. The ratio of the chain transfer agent having an active group and the chain transfer agent having an inactive group is, for example, in a range of from 1/100,000 up to 100/1 as a molar ratio of a chain transfer agent having an active group to a chain transfer agent having an inactive group.

After the completion of polymerization, the produced fine magnetic particles are separated and purified by proper methods, such as washing, filtration, decantation, precipitation fractionation, and centrifugation, to obtain a magnetic structure binding to a graft polymer containing an active group at one end thereof.

(Process for Binding Secondary Capturing Body to Active Group)

The process for binding a secondary capturing body to an active group of a magnetic structure can be carried out by a binding method using an amide bond as described above, for example. Examples of the binding method using an amide bond are as follows:

introducing a carboxyl group to an end of a graft polymer and binding the carboxyl group to an amino group of a secondary capturing body with an amide bond, or introducing an amino group to an end of a graft polymer and binding the amino group to a carboxyl group of a secondary capturing body with an amide bond. The reaction conditions for forming an amide bond, e.g., the pH and reaction temperature, may be optionally determined depending on the combination.

Figure 10:
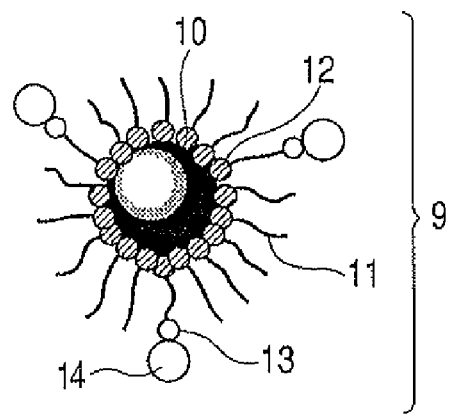
FIG. 10 is a schematic diagram illustrating a magnetic label according to an embodiment.

By conducting at least these processes, as shown in FIG. 10, a magnetic label 9 having a magnetic structure and a secondary capturing body 14 which is bound to an end of a graft polymer of the magnetic structure through an active group 13 can be obtained. Here, the magnetic structure includes a substrate 10, a living polymerization initiator group 12 borne by the substrate surface, and a graft polymer (polymer chain) 11 formed on the surface of the substrate 10 through the living polymerization initiator group 12.

EXAMPLES

The present invention will now be described in further detail with reference to Examples, but is not limited thereto. The materials, composition conditions, and reaction conditions can be freely modified within a scope of the present invention to obtain a detecting element or a detection kit achieving similar functions and effects.

The present invention will now be described in further detail by referring to Examples regarding the detection methods according to the First to Fourth Embodiments of the present invention.

Example 1

In this Example, an example according to the First Embodiment of the present invention will be described.

In this Example, PSA is detected by using a detecting element including a non-detecting part having a coating layer on the surface thereof and a detecting part having a primary antibody for capturing PSA on the surface thereof as a combination with a magnetic label including magnetite having a secondary antibody for capturing PSA on the surface thereof. In this method, the detecting part is applied with a surface potential by an external power supply. Further, the detecting element is a magnetoresistive element.

(1) Preparation of Magnetic Label

First, a magnetic label 9 having a secondary antibody for capturing PSA as a secondary capturing body 4 is prepared. Magnetite particles (average particle diameter: 50 nm) are heated under a dry $N_2$ atmosphere and are then dispersed in anhydrous toluene. To this magnetite particle/toluene dispersion liquid, aminopropyltrimethoxysilane as a silane coupling agent is added for introducing an amino group to the surfaces of the magnetite particles. In this regard, however, if the amino group is excessively introduced to the magnetite particles, the isoelectric point as magnetite is largely changed. Therefore, the amount of an amino group to be introduced is properly controlled by pretreatment (such as drying conditions) of the magnetite particles and conditions (such as concentration and mixing ratio) in silane-coupling treatment. Then, a secondary antibody, as a secondary capturing body, for capturing PSA is immobilized by chemically binding the amino group and a peptide chain by using a cross-linking agent, such as glutaraldehyde, for immobilizing the secondary antibody.

By the procedure above, a magnetic label provided with a secondary capturing body can be obtained. Since this magnetic label is composed of magnetite having an isoelectric point of about 6.5, the magnetic label is positively charged in an aqueous solution having a pH lower than this value (the acid side than 6.5).

(2) Preparation of Detecting Element

Next, a detecting element including a detecting part and a non-detecting part is prepared. The non-detecting part includes a substrate and a coating layer. The detecting part includes a primary antibody, as a primary capturing body, for capturing PSA on the surface thereof. In this Example, a magnetoresistive element shown in FIG. 11 but the upper electrode is not yet formed is used as a substrate 6 in FIG. 5. An Au film is formed on the surface of the substrate 6, and a $SiO_2$ film is formed at a region other than a region where becomes to a detecting part. That is, a substrate was formed by forming an Au film as an upper electrode at a region which is used as a detecting part of the substrate for providing a part of the detecting part and forming a $SiO_2$ film at a region which is used as a non-detecting part for providing a part of the non-detecting part.

Then, a part of the non-detecting part having the $SiO_2$ film on the surface thereof is used as a substrate and a coating layer is formed on the surface of the substrate. First, the $SiO_2$ film is immersed in anhydrous toluene, and 2-(4 chloromethylphenyl)ethyltrimethoxysilane as a silane-coupling agent is added thereto to introduce a chloromethyl group to the surface of the $SiO_2$ film. The progress of this reaction can be confirmed by XPS using Cl atoms as an indicator. Then, the $SiO_2$ film to which the chloromethyl group is introduced is immersed in water. Sodium dithiocarbamate is added thereto to react with the chloromethyl group. Thus, a polymerization-initiating point for UV graft polymerization is introduced to the surface of the $SiO_2$ film. The progress of this reaction can be confirmed by XPS using N atoms and S atoms as indicators. Then, the $SiO_2$ film is immersed in acetone, and glycydil methacrylate is added thereto. The reaction vessel is purged with nitrogen. Then, UV graft polymerization is performed with UV light of a wavelength of 312 to 577 nm irradiated by a UV lamp at room temperature for 2 hr to form a polyglycidyl methacrylate on the $SiO_2$ film surface. Then, the $SiO_2$ film is immersed in ammonium water adjusted to a pH of 11 and heated. With this reaction, an amino group is introduced to the polyglycidyl methacrylate on the $SiO_2$ film surface. The reaction can be confirmed by XPS by using N atoms as an indicator.

With the above described procedures, a non-detecting part 8 having a coating layer 16 on the surface thereof can be obtained. Here, the coating layer is a hydrophilic layer formed of a graft layer of polyglycidyl methacrylate and therefore is excellent in prevention of non-specific adsorption of many kinds of proteins and is readily positively charged in an aqueous solution because of its amino group.

Then, a primary antibody, as a primary capturing body 3, for capturing PSA is immobilized on the surface of the Au film which is a region serving as a detecting part. First, an ethanol solution of 10-carboxy-1-decanethiol is applied to the surface of the Au film. With this procedure, a carboxyl group is immobilized on the Au film surface. Then, N-hydroxysulfosuccinimide aqueous solution and 1-ethyl-3-(3-dimethylaminopropyl)carbodiimide hydrochloride aqueous solution are similarly applied to the Au film surface. With these procedures, the carboxyl group immobilized on the Au film surface is transformed into succinimide. The primary antibody, as the primary capturing body, for capturing PSA can be immobilized by reacting the succinimide group with the amino group of the primary capturing body. Further, the unreacted succinimide group on the Au film surface may be removed by the addition of hydroxylamine hydrochloride.

With the above-described procedures, a detecting element including a non-detecting part 8 having a coating layer 16 of polyglycidyl methacrylate and a detecting part 7 having a primary antibody, as a primary capturing body 3, for capturing PSA on the surface thereof can be prepared.

Figure 11:
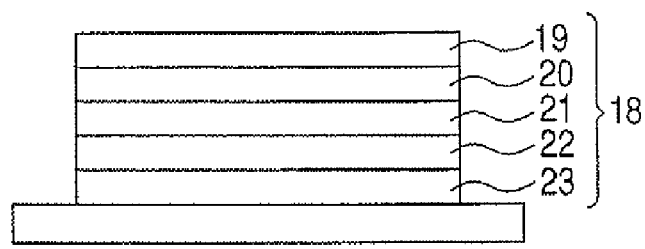
FIG. 11 is a schematic diagram illustrating a magnetoresistive element according to an embodiment.

In FIG. 11, the reference numeral 18 denotes a magnetoresistive element, 19 upper electrode, 20 free layer, 21 tunnel barrier film, 22 pin layer, and 23 lower electrode.

(3) Detection of PSA

The detection of PSA, which is known as a prostate cancer marker, can be performed by the following processes using the magnetic label and the detecting element prepared in the above (1) and (2).

Figure 8:
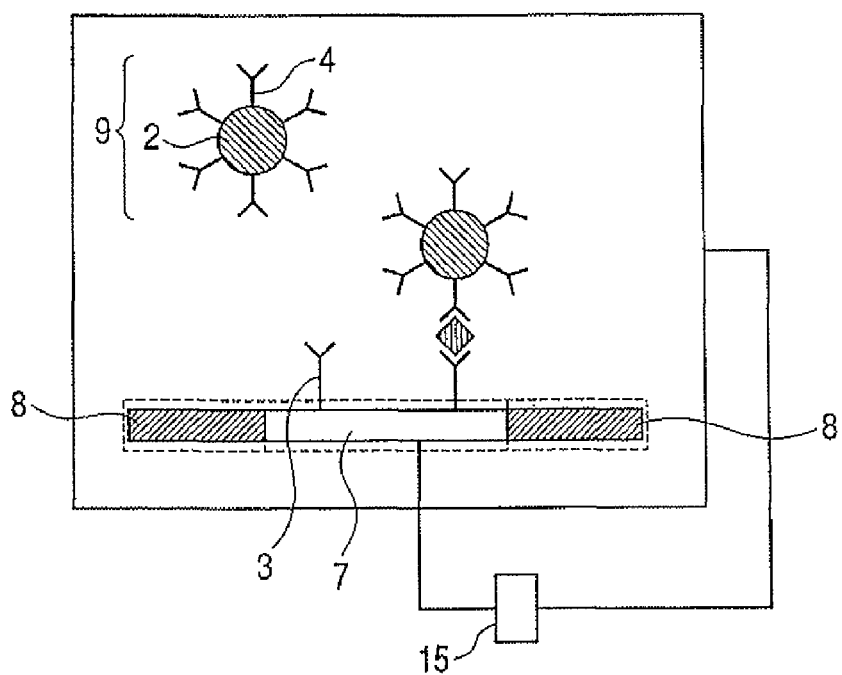
FIG. 8 is a schematic diagram illustrating a detecting element and magnetic label in Example 1.

(a) a phosphate buffer (pH 7.0) containing an antigen (target substance), i.e., PSA, is brought into contact with a detecting part of the detecting element;
(b) unreacted PSA is washed out with a phosphate buffer;
(c) a phosphate buffer (pH 5.5) containing a magnetic label is brought into contact with the detecting part of the detecting element after the completion of the processes (a) and (b), and a current or voltage is applied to the detecting part by an external power supply 15 connected to the detecting part 7 as shown in FIG. 8 so that the surface potential of the detecting part surface becomes zero; and
(d) unreacted magnetic label is washed out with a phosphate buffer and the application of the voltage or current by the external power supply is stopped.

With these procedures, PSA as a target substance is captured by the primary antibody to PSA and the secondary antibody to PSA wherein the primary and secondary antibodies are present on the surfaces of the detecting part and the magnetic label, respectively, so that the magnetic label is immobilized in the vicinity of the detecting part of the detecting element, as shown in FIG. 5.

When the target substance is not present in a sample solution, the magnetic label does not stay in the vicinity of the detecting part of the detecting element. Therefore, the target substance can be detected by detecting the presence or absence of the magnetic label. Further, by previously preparing a calibration curve showing a relationship between the magnetic label and the number of the target substance, the amount of the target substance contained in a sample solution can be indirectly determined based on the number of the magnetic label.

Further, in the process (c) of this Example, since the pH of the used buffer is 5.5 which is acidic than the isoelectric point of magnetite, the magnetic label is positively charged. In addition, the non-detecting part has polyglycidyl methacrylate containing a large number of amino groups on the surface thereof and thereby is positively charged in an aqueous solution of a pH of about 10 or less. Therefore, the surface of the non-detecting part is also positively charged. Furthermore, the surface of the detecting part is adjusted by an external power supply so as to be zero in surface potential. Therefore, a repulsive force is generated between the magnetic label and the non-detecting part. Consequently, the detection efficiency is improved. Here, in FIG. 8, since an insulating film of $SiO_2$ film is formed on the surface of a region serving as the non-detecting part, a surface potential is imparted to the surface of the detecting part 7 only by applying a voltage or current to the substrate. In addition, the surface potential of only the detecting part 7 can be controlled by forming an electrode at an area which opposes the detecting part 7 with the substrate 1 therebetween and applying a current or voltage.

Example 2

In this Example, an example different from Example 1 according to the First Embodiment will be described.

In this Example, PSA is detected by using a detecting element including a non-detecting part having a coating layer and a detecting part having a primary antibody capturing PSA as a combination with a magnetic label including a coating layer and a magnetite provided with a secondary antibody for capturing PSA. This Example is the same as Example 1 except that the magnetic label has a coating layer.

(1) Preparation of Magnetic Label

First, a magnetic structure 2 having a coating layer 16 on the surface thereof is prepared. Magnetite particles are heated under a dry $N_2$ atmosphere and are then dispersed in anhydrous toluene. To this magnetite particle/toluene dispersion liquid, 2-(4-chloromethylphenyl)ethyltrimethoxysilane as a silane-coupling agent is added for introducing a chloromethyl group to the magnetite particles. This reaction can be confirmed by detecting Cl atoms by XPS. The magnetite particles to which chloromethyl group is introduced are dispersed in water. Sodium dithiocarbamate is added thereto for the reaction with the chloromethyl group. Thus, an initiating point for UV graft polymerization is introduced to the surfaces of the magnetite particles. This reaction can be confirmed by detecting N atoms and S atoms by XPS. Then, the magnetite particles and acetone are weighed into a reaction vessel and the magnetite particles are dispersed in the acetone by sonication. Then, glycydil methacrylate is weighed into the reaction vessel, and the reaction vessel is purged with nitrogen. Then, UV graft polymerization is performed with UV light of a wavelength of 312 to 577 nm irradiated by a UV lamp at room temperature for 2 hr to form polyglycidyl methacrylate on the surfaces of the magnetite particles. This reaction can be confirmed by an increase in the particle diameters measured by a dynamic light scattering method.

Then, a secondary antibody 4 for capturing PSA is immobilized to a magnetic structure 2 having the coating layer 16 on the surface thereof. First, the magnetic structure is dispersed in water, and aminoethanethiol and dithiothreitol are added thereto. The resulting mixture is adjusted to a pH of 5 with a hydrochloride aqueous solution or a sodium hydroxide aqueous solution for reaction. With this, an amino group and a thiol group are introduced to the surface of the coating layer of the magnetic structure. Then, N-succinimidyl 3-(2-pyridyldithio)propionate is added to the mixture and reacted at room temperature for 5 hr to introduce a succinimide group to the magnetic structure surface via the thiol group. The succinimide group is reacted with an amino group of an antibody to immobilize the secondary antibody for capturing PSA a secondary capture component.

With the above-described procedures, a magnetic label including a coating layer of polyglycidyl methacrylate and magnetite provided with a secondary antibody for capturing PSA can be prepared.

In addition, the coating layer is a hydrophilic layer formed of a graft layer of polyglycidyl methacrylate and therefore is excellent in prevention of non-specific adsorption of many kinds of proteins and is readily positively charged in an aqueous solution because of its amino group.

(2) Preparation of Detecting Element

A detecting element having a detecting part and a non-detecting part, wherein the non-detecting part is provided with a non-detecting part coating layer and the detecting part is provided with a primary antibody for capturing PSA as a primary capturing body, is prepared by the same method as that in Example 1.

(3) Detection of PSA

The detection of PSA, which is known as a prostate cancer marker, can be performed by using the magnetic label and the detecting element according to the following processes. In this Example, the detecting part is connected to an external power supply for controlling the surface potential of the detecting part as in Example 1.

Figure 9:
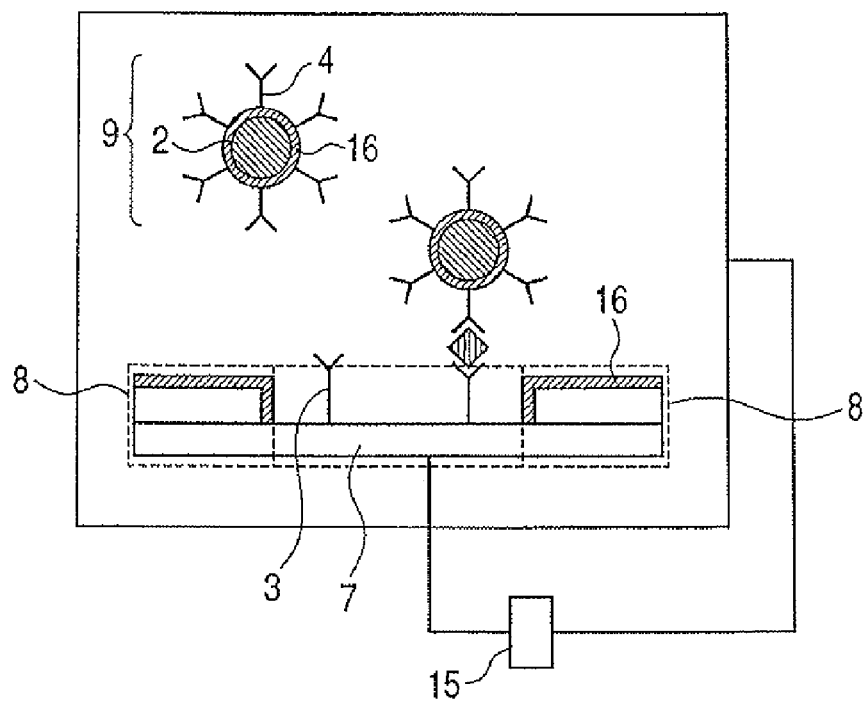
FIG. 9 is a schematic diagram illustrating a detecting element and magnetic label in Examples 2 to 5.

(a) a phosphate buffer (pH 7.0) containing an antigen (target substance), i.e., PSA, is brought into contact with a detecting part of the detecting element;
(b) unreacted PSA is washed out with a phosphate buffer;
(c) a phosphate buffer (pH 5.5) containing a magnetic label is brought into contact with the detecting part of the detecting element after the completion of the processes (a) and (b), and a current or voltage is applied to the detecting part by an external power supply 15 connected to the detecting part 7 as shown in FIG. 9 so that the surface potential of the detecting part surface becomes zero; and
(d) unreacted magnetic label is washed out with a phosphate buffer and the application of the voltage or current by the external power supply is stopped.

With these procedures, PSA as a target substance is captured by the primary antibody to PSA and the secondary antibody to PSA wherein the primary and secondary antibodies are present on the surfaces of the detecting part and the magnetic label, respectively, so that the magnetic label 9 is immobilized in the vicinity of the detecting part 7 of the detecting element as shown in FIG. 6.

In the process (c) of this Example, since the pH of the used buffer is 5.5 and the magnetic label and the non-detecting part have polyglycidyl methacrylate containing a large number of amino groups on the surfaces thereof, the magnetic label and the non-detecting part are positively charged. Further, the surface potential of the detecting part surface is controlled to zero by an external power supply. With this, a repulsive force is generated between the non-detecting part and the magnetic label. Consequently, the detection efficiency can be improved.

In addition, in this Example, since the magnetic label and the non-detecting part are provided with the respective coating layers which are formed of substantially the same material, the polarity of the surface potential of the magnetic label and the polarity of the surface potential of the non-detecting part tend to be the same even if a buffer having an arbitrary pH value is used in the process (c). Thus, the effect of the present invention can be obtained.

Example 3

In this Example, an example according to the Fourth Embodiment of the present invention will be described.

In this Example, PSA is detected by using a detecting element including a non-detecting part having a coating layer and a detecting part having a primary antibody for capturing PSA and enable to be imparted with a surface potential by an external power supply as a combination with a magnetic label including a coating layer and a magnetite provided with a secondary antibody for capturing PSA. This Example is the same as Example 2 except that a negative surface potential is imparted to the detecting part by an external power supply.

(1) Preparation of Magnetic Label

A magnetic label is prepared by the same method as that in Example 2.

(2) Preparation of Detecting Element

A detecting part 7 provided with a primary antibody for capturing PSA and a non-detecting part 8 having a coating layer 16 on the surface thereof are prepared by the same method as that in Example 1.

(3) Detection of PSA

The detection of PSA, which is known as a prostate cancer marker, can be performed by using the magnetic label and the detecting element according to the following processes.

(a) a phosphate buffer (pH 7.0) containing an antigen (target substance), i.e., PSA, is brought into contact with a detecting part 7 of the detecting element;
(b) unreacted PSA is washed out with a phosphate buffer;
(c) a phosphate buffer (pH 5.5) containing a magnetic label is brought into contact with the detecting part of the detecting element after the completion of the processes (a) and (b), and a current or voltage is applied to the detecting part by an external power supply 15 which is connected to the detecting part 7 as shown in FIG. 9 so that the surface potential of the detecting part surface becomes a negative potential; and
(d) unreacted magnetic label is washed out with a phosphate buffer and the application of the voltage or current by the external power supply is stopped.

With these procedures, PSA as a target substance is captured by the primary antibody to PSA and the secondary antibody to PSA wherein the primary and secondary antibodies are present on the surfaces of the detecting part and the magnetic label, respectively, so that the magnetic label is immobilized in the vicinity of the detecting part of the detecting element as shown in FIG. 6.

In the process (c) of this Example, since the pH of the used buffer is 5.5 and the magnetic label and the non-detecting part have polyglycidyl methacrylate containing a large number of amino groups on the surfaces thereof, the magnetic label and the non-detecting part are positively charged. Further, the surface potential of the detecting part surface can be controlled to a negative potential by an external power supply. With this, a repulsive force is generated between the non-detecting part and the magnetic label and an electrostatic attractive force is generated between the detecting part and the magnetic label. Consequently, the detection efficiency can be improved.

In this Example, as in Example 2, the non-detecting part and the magnetic label are provided with the respective coating layers which are formed of substantially the same material. Therefore, the surface potentials of the non-detecting part and the magnetic label can be adjusted to negative potentials and the surface potential of the detecting part surface can be adjusted to a positive potential by changing the pH of a buffer and the surface potential of the detecting part.

Example 4

In this Example, an example according to the Second Embodiment of the present invention will be described.

In this Example, PSA is detected by using a detecting element including a non-detecting part having a coating layer and a detecting part having a primary antibody for capturing PSA and enable to be imparted with a surface potential by an external power supply as a combination with a magnetic label including a coating layer and a magnetite provided with a secondary antibody for capturing PSA. The detecting part is imparted with a surface potential by the external power supply. In addition, the detecting element employs a magnetoresistive element.

(1) Preparation of Magnetic Label

A magnetic label is prepared by the same method as that in Example 2.

(2) Preparation of Detecting Element

As in Example 1, an Au film is partially formed on a substrate surface and a $SiO_2$ film is formed at a region other than a region used as the detecting part. That is, on a substrate, an Au film is formed at a region which is used as the detecting part and a $SiO_2$ film is formed at a region which is used as the non-detecting part.

In this Example, a non-detecting part provided with a coating layer of a PHEMA layer is prepared.

First, a $SiO_2$ film is immersed in anhydrous toluene so that a hydroxyl group of the $SiO_2$ film reacts with a functional group of a precursor of an atom transfer radical polymerization initiator group according to reaction formula (I). Thus, the atom transfer radical polymerization initiator group is introduced to the surface of the non-detecting part.

Then, the non-detecting part introduced with the atom transfer radical polymerization initiator group is immersed in methanol, and ethyl 2-bromoisobutyrate as a free polymerization initiator is added thereto and CuBr, 2,2'-bipyridyl is further added thereto. Oxygen in the reaction system is removed by freeze vacuum degassing, and then the reaction system is purged with nitrogen, followed by the atom transfer radical polymerization of an HEMA (2-hydroxyethyl methacrylate) monomer for a predetermined period of time. Further, the molecular weight and a molecular weight distribution of PHEMA generated from ethyl 2-bromoisobutyrate added as a free polymerization initiator are measured to confirm that PHEMA has a number average molecular weight of 60,000 and a molecular weight distribution of 1.07. With these results, the graft polymer grafted on the non-detecting part is confirmed to be a polymer having a uniform chain length. The film thickness and weight of the graft polymer grafted on the non-detecting part are measured to confirm that the graft polymer has a graft density of 0.6 molecules/$nm^2$.

With the above-described procedures, a non-detecting part coating layer can be formed on the surface of a non-detecting part. The PHEMA layer is a hydrophilic layer having a large number of hydroxyl groups and is excellent in prevention of non-specific adsorption of many kinds of proteins.

Further, in this Example, a detecting part provided with a primary antibody for capturing PSA is prepared by the same method as that in Example 2.

(3) Detection of PSA

The detection of PSA, which is known as a prostate cancer marker, can be performed by using the magnetic label and the detecting element according to the following processes.

(a) a phosphate buffer (pH 7.0) containing an antigen (target substance), i.e., PSA, is brought into contact with a detecting part of the detecting element;
(b) unreacted PSA is washed out with a phosphate buffer;
(c) a phosphate buffer having a pH near the isoelectric point of PHEMA forming a coating layer of a non-detecting part and containing a magnetic label is brought into contact with the detecting part of the detecting element after the completion of the processes (a) and (b), and a current or voltage is applied to the detecting part by an external power supply 15 which is connected to the detecting part 7 as shown in FIG. 9 so that the surface potential of the detecting part surface becomes a negative potential; and
(d) unreacted magnetic label is washed out with a phosphate buffer and the application of the voltage or current by the external power supply is stopped.

With these procedures, PSA as a target substance is captured by the primary antibody to PSA and the secondary antibody to PSA wherein the primary and secondary antibodies are present on the surfaces of the detecting part and the magnetic label, respectively, so that the magnetic label is immobilized in the vicinity of the detecting part of the detecting element as shown in FIG. 6.

In the process (c) of this Example, since a buffer having a pH near the isoelectric point (near neutral) of PHEMA which forms a coating layer of a non-detecting part is used, the surface of the non-detecting part is actually electrically neutral. Further, the surface potential of the detecting part surface can be controlled to a negative potential by an external power supply. In addition, the magnetic label has polyglycidyl methacrylate containing a large number of amino groups on the surface thereof and thereby is positively charged in a near neutral condition. With this, an electrostatic attractive force is generated between the detecting part and the magnetic label. Consequently, the detection efficiency can be improved.

Example 5

In this Example, an example according to the Third Embodiment of the present invention will be described.

In this Example, PSA is detected by using a detecting element including a non-detecting part having a coating layer and a detecting part having a primary antibody for capturing PSA and enable to be imparted with a surface potential by an external power supply as a combination with a magnetic label including magnetite provided with a secondary antibody for capturing PSA. The detection is carried out as in Example 2 except that the pH of a buffer solution for a sample containing a magnetic label is adjusted to a value higher than the isoelectric point of a magnetic structure and that the absolute value of the surface potential of the detecting part surface is larger than that of the non-detecting part and both surface potentials are positive.

(1) Preparation of Magnetic Label

A magnetic label is prepared by the same method as that in Example 1.

(2) Preparation of Detecting Element

A detecting part provided with a primary antibody for capturing PSA and a non-detecting part provided with a non-detecting part coating layer are prepared by the same method as that in Example 2.

(3) Detection of PSA

The detection of PSA, which is known as a prostate cancer marker, can be performed by using the magnetic label and the detecting element according to the following processes.

(a) a phosphate buffer (pH 7.0) containing an antigen (target substance), i.e., PSA, is brought into contact with a detecting part of the detecting element;
(b) unreacted PSA is washed out with a phosphate buffer;
(c) a phosphate buffer (pH 7.5) containing a magnetic label is brought into contact with the detecting part of the detecting element after the completion of the processes (a) and (b), and a current or voltage is applied to the detecting part by an external power supply 15 connected to the detecting part 7 as shown in FIG. 9 so that the surface potential of the detecting part surface becomes a positive potential; and (d) unreacted magnetic label is washed out with a phosphate buffer and the application of the voltage or current by the external power supply is stopped.

With these procedures, PSA as a target substance is captured by the primary antibody to PSA and the secondary antibody to PSA wherein the primary and secondary antibodies are present on the surfaces of the detecting part and the magnetic label, respectively, so that the magnetic label is immobilized in the vicinity of the detecting part of the detecting element as shown in FIG. 6.

In the process (c) of this Example, since the pH of the used buffer is 7.5 which is basic than the isoelectric point of the magnetite, the magnetic label is negatively charged. In addition, since the non-detecting part has polyglycidyl methacrylate containing a large number of amino groups on the surface thereof, the non-detecting part is positively charged at pH 7.5. The detecting part is also positively charged by an external power supply. However, the detecting part is imparted with a surface potential larger than that of the non-detecting part by the external power supply. Therefore, the electrostatic attractive force between the detecting part and the magnetic label is larger than that between the nondetecting part and the magnetic label. Consequently, the detection efficiency is improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2006-100683, filed Mar. 31, 2006, and No. 2006-317401, filed Nov. 24, 2006, which are hereby incorporated by reference herein in their entirety.

The invention claimed is:

1. A method for detecting a target substance in a sample solution, comprising:
   a first step of preparing a detecting element comprising a detecting part and a non-detecting part, and a magnetic label including the target substance, the detecting part including a primary capturing body on the surface thereof;
   a second step of capturing the target substance of the magnetic label with the primary capturing body; and
   a third step of detecting the magnetic label present in the vicinity of the detecting part,
   wherein the surface potential $\psi_1$ of the magnetic label in the second step, the surface potential $\psi_2$ of the detecting part, and the surface potential $\psi_3$ of the non-detecting part satisfy any one of the following relationships i) to iv) by forming a layer on a surface of at least one of the magnetic label, the detecting part, and the non-detecting part in the first step:

$\psi_1\psi_3>0$ and $\psi_2=0$,　　　i)

$\psi_1\psi_2<0$ and $\psi_3=0$,　　　ii)

$\psi_1\psi_2<0$, $\psi_2\psi_3>0$, and $|\psi_2|>|\psi_3|$, and　　　iii)

$\psi_1\psi_2<0$ and $\psi_2\psi_3<0$, and　　　iv)

wherein the magnetic label and the non-detecting part each have a layered structure, and the outermost layer of the layered structure forming the magnetic label and the outermost layer of the layered structure forming the non-detecting part are made of the same material.

2. The method for detecting a target substance according to claim 1, wherein the layers made of the same material are formed of a graft polymer.

3. A method for detecting a target substance in a sample solution, comprising:
   a first step of preparing a detecting element comprising a detecting part and a non-detecting part, and a magnetic label including a secondary capturing body, the detecting part including a primary capturing body on the surface thereof;
   a second step of capturing the target substance with the secondary capturing body of the magnetic label after capturing the target substance with the primary capturing body; and
   a third step of detecting the magnetic label present in the vicinity of the detecting part,
   wherein the surface potential $\psi_1$ of the magnetic label in the second step, the surface potential $\psi_2$ of the detecting part, and the surface potential $\psi_3$ of the non-detecting part satisfy any one of the following relationships i) to iv) by forming a layer on a surface of at least one of the magnetic label, the detecting part, and the non-detecting part in the first step:

$\psi_1\psi^3>0$ and $\psi_2=0$,　　　i)

$\psi_1\psi_2<0$ and $\psi_3=0$,　　　ii)

$\psi_1\psi_2<0$, $\psi_2\psi_3>0$, and $|\psi_2|>|\psi_3|$, and　　　iii)

$\psi_1\psi_2<0$ and $\psi_2\psi_3<0$, and　　　iv)

wherein the magnetic label and the non-detecting part each have a layered structure, and the outermost layer of the layered structure forming the magnetic label and the outermost layer of the layered structure forming the non-detecting part are made of the same material.

4. The method for detecting a target substance according to claim 3, wherein the layers made of the same material are formed of a graft polymer.

* * * * *